(12) United States Patent  
Sharkey et al.

(10) Patent No.: US 10,751,189 B2  
(45) Date of Patent: Aug. 25, 2020

(54) RESECTION GUIDE, TRIAL KNEE JOINT IMPLANT, AND SURGICAL INSTRUMENT FOR KNEE ARTHROPLASTY

(71) Applicant: CORENTEC CO. LTD., Chungcheongnam-do (KR)

(72) Inventors: Peter F. Sharkey, Villanova, PA (US); Javad Parvizi, Gladwyne, PA (US)

(73) Assignee: CORENTEC CO., LTD, Cheonan-si, Chungcheongnamodo (KR)

( * ) Notice: Subject to any disclaimer, the term of this patent is extended or adjusted under 35 U.S.C. 154(b) by 284 days.

(21) Appl. No.: 15/720,820

(22) Filed: Sep. 29, 2017

(65) Prior Publication Data

US 2018/0098773 A1    Apr. 12, 2018

Related U.S. Application Data

(60) Provisional application No. 62/407,316, filed on Oct. 12, 2016.

(51) Int. Cl.

| | |
|---|---|
| *A61B 17/58* | (2006.01) |
| *A61B 17/15* | (2006.01) |
| *A61F 2/38* | (2006.01) |
| *A61F 2/46* | (2006.01) |
| *A61F 2/30* | (2006.01) |
| *A61B 17/17* | (2006.01) |
| *A61B 17/88* | (2006.01) |
| *A61B 17/02* | (2006.01) |

(52) U.S. Cl.
CPC .......... *A61F 2/3886* (2013.01); *A61B 17/154* (2013.01); *A61B 17/155* (2013.01); *A61B 17/157* (2013.01); *A61B 17/1764* (2013.01); *A61F 2/30771* (2013.01); *A61F 2/38* (2013.01); *A61F 2/389* (2013.01); *A61F 2/3859* (2013.01); *A61F 2/46* (2013.01); *A61F 2/4684* (2013.01); *A61B 17/88* (2013.01); *A61B 2017/0268* (2013.01); *A61F 2002/30606* (2013.01); *A61F 2002/30883* (2013.01); *A61F 2002/3895* (2013.01)

(58) Field of Classification Search
CPC ...... A61F 2/3886; A61F 2/30771; A61F 2/38; A61F 2/3859; A61F 2/389; A61F 2/46; A61F 2/4684; A61F 2002/30606; A61F 2002/30883; A61F 2002/3895; A61B 17/154; A61B 17/155; A61B 17/157; A61B 17/1764; A61B 17/88
USPC ............ 606/87–90; 623/13.12–13.16, 20.14, 623/20.32, 20.35
See application file for complete search history.

(56) References Cited

U.S. PATENT DOCUMENTS

| | | | | |
|---|---|---|---|---|
| 4,211,228 | A * | 7/1980 | Cloutier | A61F 2/389 606/102 |
| 5,037,423 | A * | 8/1991 | Kenna | A61B 17/155 606/86 R |
| 7,094,241 | B2 * | 8/2006 | Hodorek | A61B 17/154 606/87 |

(Continued)

*Primary Examiner* — Jessica Weiss  
(74) *Attorney, Agent, or Firm* — Workman Nydegger

(57) ABSTRACT

Disclosed is a resection guide, a trial knee joint implant, and a surgical instrument for knee arthroplasty. The resection guide, the trial knee joint implant, and the surgical instrument enable implantation of an implant that provides improved vertical fixing force and initial fixing force as compared with an existing cementless or uncemented implant.

20 Claims, 24 Drawing Sheets

(56) References Cited

U.S. PATENT DOCUMENTS

| | | | | |
|---|---|---|---|---|
| 8,167,888 B2* | 5/2012 | Steffensmeier | A61B 17/1764 | 606/86 R |
| 2002/0198530 A1* | 12/2002 | Sanford | A61B 17/154 | 606/87 |
| 2004/0097951 A1* | 5/2004 | Steffensmeier | A61B 5/1071 | 606/102 |
| 2006/0111726 A1* | 5/2006 | Felt | A61F 2/30721 | 606/86 R |
| 2010/0249788 A1* | 9/2010 | Roche | A61B 5/1076 | 606/87 |
| 2011/0004316 A1* | 1/2011 | Murray | A61B 17/1764 | 623/20.3 |
| 2012/0259335 A1* | 10/2012 | Scifert | A61B 17/155 | 606/80 |
| 2013/0035694 A1* | 2/2013 | Grimm | A61B 2/4657 | 606/102 |
| 2015/0374386 A1* | 12/2015 | Collazo | A61B 17/1675 | 623/20.35 |

* cited by examiner

Small

Medium

Large

RESECTION GUIDE, TRIAL KNEE JOINT IMPLANT, AND SURGICAL INSTRUMENT FOR KNEE ARTHROPLASTY

CROSS-REFERENCE TO RELATED APPLICATIONS

This application claims the benefit of U.S. Provisional Application No. 62/407,316, filed Oct. 12, 2016, which is incorporated herein by specific reference.

FIELD OF THE INVENTION

The present invention relates generally to a resection guide, a trial knee joint implant, and a surgical instrument for knee arthroplasty. More particularly, the present invention relates to a resection guide, a trial knee joint implant, and a surgical instrument for knee arthroplasty, all of which enable implantation of an implant providing improved vertical fixing force and initial fixing force in comparison with conventional cementless or uncemented implants.

DESCRIPTION OF THE RELATED ART

A knee joint refers to a joint formed between three bones: a femur, a tibia, and a patella. Knee joints are provided in the left and right legs support a body's weight and are essential for leg-involved movements such as walking and running. Since the knee joint is frequently used and is likely to be overworked, the number of patients with knee joints that are incurably damaged is gradually increasing due to wear of knee joints, aging of bone tissues, accidents, and the like.

Disease symptoms of the knee joint may appear without any particular external injury, and its cause is mainly structural and functional abnormality in a patellofemoral joint. Osteomalacia of articular cartilage may be caused by repetitive application of excessive forces to the patellofemoral joint when legs are abnormally bent outward or feet are severely turned out. A problem such as weakening of a quadriceps femoris muscle is likely to occur when knee joints are not used for a long period of time.

A treatment, such as an orthosis that can stabilize the knee joint, may be used when there is structural abnormality in a patellofemoral joint. However, when the damage is severe, another treatment, for example, a surgical treatment that replaces a native knee joint with an artificial knee joint may be employed. Recently, a surgical procedure for replacing an incurably damaged knee joint with an artificial knee joint has been widely performed. There are two types of surgical procedures for a knee joint replacement: uni-compartmental knee arthroplasty (UKA) and total knee arthroplasty (TKA), which are distinguished by the amount of a knee joint that is replaced with an artificial implant. Bicruciate retaining (BCR) TKA is one type of TKA, where an anterior cruciate ligament (ACL) is preserved. BCR TKA has advantages of natural knee motion, an improved range of motion (ROM), and improved joint functions.

UKA has advantages over TKA in terms of lower morbidity and mortality, higher bone preservation, more rapid recovery, shorter hospital stay, and excellent implant functions. However, a revision rate of UKA is approximately five times higher than that of TKA. Also, aseptic loosening, unexplained pain, and an implant-Poly Methyl Methacrylate (PMMA) construction that provides insufficient support for forces generated by patient activities and body habitus are posed as disadvantages.

Due to limited exposure and lack of access to the posterior side of the knee, using an optimal cement technique is challenging. Also, since surgeons often use a limited amount of PMMA during UKA, initial implant fixation is less than optimal. For these reasons, cementless UKA is relatively advantageous. In particular, uncemented implant fixation of cementless UKA can cause bone remodeling concomitant with structural enhancement and reduce a possibility of aseptic loosening caused by bone failure. Moreover, the cementless UKA achieves bone ingrowth over a wide implant surface to prevent concentration of forces and improves resistance to loosening. Such advantages of cementless or uncemented UKA also apply to TKA.

Since many advantages, such as extended durability, short surgery time, potential bone preservation, and elimination of PMMA which may lead to embolism of bone marrow, are known, uncemented UKA/TKA is rapidly gaining popularity.

However, despite the many advantages, the cementless or uncemented UKA and TKA still have room for improvement. FIGS. 1 to 7 show problems with conventional uncemented UKA and TKA. It can be understood based on the drawings that it is difficult to ensure stable initial implant fixation.

In an existing TKA tibial component 30, a keel 32 provides excellent rotational stability, whereas coronal plane stability provided by the keel 32 is unsatisfactory due to the keel being vulnerable to forces exerted vertically as shown in FIG. 1, and it is even more difficult to obtain saggital plane stability due to the rollback as illustrated in FIG. 2.

Such difficulties are also presented in a UKA tibial component 40 as shown in FIGS. 3A and 3B because fixation pegs 42 are arranged parallel to rocking force. Moreover, as illustrated in FIG. 4, in the case of a UKA femoral component 50, since forces applied to a joint are parallel to fixation pegs 52, the UKA femoral component 50 is likely to perform rocking motion, leading to bone ingrowth failure.

FIG. 5 is a schematic view illustrating a method of loading a tibial component 30 serving as a knee joint implant. Since the tibial component 30 is loaded from the top, the tibia must be dislocated as illustrated in FIG. 5, leading to a complicated and invasive surgical procedure.

As illustrated in FIGS. 6A and 6B, when the tibial component 30 is removed for revision surgery, a metal plate on the surface of the tibia restricts access to the keel 32, makes cutting through the keel 32 challenging, and generates a significant amount of metal debris. In such a case, substantial bone loss is accompanied when the tibial component 30 is forcefully extracted.

Bicruciate retaining (BCR) TKA is one type of TKA, where an anterior cruciate ligament (ACL) is preserved. BCR TKA has advantages of natural knee motion, an improved range of motion (ROM), and improved joint functions. Since 70 to 80 percent of patients who receive TKA have normal anterior cruciate ligaments, removal of the normal anterior cruciate ligaments is undesirable and a BCR tibial component is thus used. However, an existing BCR tibial component 300 requires formation of a cruciate bone island 1000 as illustrated in FIG. 7. Since the cruciate bone island 1000 has sharp corners (denoted by an arrow) attributable to resection of an articular surface, stress on the corners increases, thereby often causing avulsion fracture of a bone.

Accordingly, needs for developing a knee joint implant and a surgical implant for a knee joint implant capable of resolving aforementioned issues, providing stable fixing force, and reducing an amount of bone removed, are growing.

SUMMARY OF THE INVENTION

The present invention has been made in an effort to solve the problems occurring in the related art.

An objective of the present invention is to provide a resection guide enabling implantation of an implant providing stable fixing force by having high resistance to rotation and to external forces on a coronal plane and a sagittal plane.

Another objective of the present invention is to provide a resection guide enabling implantation of an implant for a knee joint, the implant allowing a small incision by being slidingly loaded from an anterior side or a lateral or medial side of a bone, thereby simplifying a surgical procedure and minimizing bone loss during removal of a bone in a revision procedure.

A further objective of the present invention is to provide a resection guide that guides resection of a bone such that a drill hole formed in the bone is partially resected and the remaining portion of the drill hole is exposed on a resected surface of the bone, wherein the remaining portion of the drill hole serves as a sliding groove and a knee joint implant is loaded in the sliding groove in a sliding manner.

A yet further objective of the present invention is to provide a resection guide that guides movement of a resection device that resects a bone, wherein a main body of the resection guide is fixed to the bone by a fixing pin that has an auxiliary function of aiding guiding of the resection device.

A yet further objective of the present invention is to provide a trial knee joint implant serving as a trial implant during arthroplasty for implanting a knee joint implant and being combined with a surgical instrument such as a resection guide during the arthroplasty, thereby simplifying a complicated surgical procedure.

A yet further objective of the present invention is to provide a surgical instrument for knee arthroplasty, the surgical instrument facilitating resection of a femur and formation of a sliding groove.

A yet further objective of the present invention is to provide a surgical instrument for knee arthroplasty, the surgical instrument facilitating checking of a gap between a distal end of a femur and a proximal end of a tibia and arrangement of a resection guide used for resection of the tibia.

A yet further objective of the present invention is to provide a surgical instrument for knee arthroplasty, the surgical instrument facilitating checking of a gap between a femur and a tibia and alignment of the femur and tibia during a surgical operation.

A yet further objective of the present invention is to provide a resection guide, a trial knee joint implant, and a surgical instrument for knee arthroplasty, all of which enable implantation of an implant having a protrusion that protrudes from a contact surface of the implant, which is to come into contact with a resected surface of a bone, wherein the protrusion engages with a sliding groove formed in the resected surface of the bone and has a portion expanded in a direction perpendicular to a direction in which the protrusion protrudes, thereby having convex-curved surfaces, whereby the protrusion has an overall circular cylinder shape, thereby preventing concentration of stress and ensuring stable fixing force without causing damage to a bone.

In order to accomplish the above objectives, the present invention is implemented by embodiments described below.

According to a first aspect of the present invention, a resection guide includes a main body with a guide portion formed to pass through the main body, the guide portion including a slot that guides movement of a resection device and a pin insertion hole that is formed to communicate with the slot and into which a fixing pin is inserted.

Preferably, in the resection guide, the pin insertion hole includes a first portion that abuts on a periphery of the slot, thereby communicating with an opening formed in the periphery of the slot, and having a width that increases as a distance to a boundary between the first portion and the slot increases.

Preferably, in the resection guide, the pin insertion hole further includes a second portion having a width that decreases as a distance to the first portion increases.

Preferably, the first portion and second portion have curved inner peripheral surfaces.

Preferably, in the resection guide, the curved inner peripheral surfaces may form an overall circular cylinder shape.

Preferably, the resection guide may further include a fixing pin having a complementary shape to the pin insertion hole and being penetrated into a bone through the pin insertion hole, thereby fixing a position of the main body.

Preferably, in the resection guide, the fixing pin may have a flat surface portion that closes an open portion of a periphery of the pin insertion hole when the fixing pin is inserted through the pin insertion hole.

Preferably, the resection guide may be used to guide resection of an proximal end of a tibia, the slot may transversely extend in the main body to guide the resection device such that the resection device moves toward a lateral side or a medial side of the tibia, with the main body being arranged on an anterior surface of the tibia, and the pin insertion hole is formed at a distal side of the slot.

Preferably, in the resection guide, the main body may include a window that is formed to pass through the main body and which is disposed at a proximal side of the slot.

Preferably, the resection guide may be used to guide resection of a distal end of a femur, the slot may include a first slot vertically extending in the main body to guide the resection device that resects the distal end of the femur, with the main body being arranged on a medial surface or a lateral surface of the femur, and the pin insertion hole may include a first pin insertion hole that abuts on a proximal periphery of the first slot, thereby communicating with an opening formed in the proximal periphery of the first slot.

Preferably, in the resection guide, the slot may include a second slot extending toward a posterior side from a lower end of the first slot, and the pin insertion hole may further include a second pin insertion hole that abuts on a proximal periphery of the second slot, thereby communicating with an opening formed in the proximal periphery of the second slot.

According to another aspect of the present invention, there is provided a trial knee joint implant including: a body portion having an articular surface and a contact surface disposed on the opposite side of the articular surface; and a protrusion protruding outward from the contact surface and having a portion expanded sideways, wherein the body portion is provided with a guide hole extending in an anterior-posterior direction of the body portion.

Preferably, in the trial knee joint implant, the protrusion may include a first portion being gradually expanded in a direction perpendicular to a direction in which the protrusion protrudes and a second portion being gradually constricted such that a width thereof gradually decreases as a distance to the first portion increases.

Preferably, in the trial knee joint implant, the first portion and the second portion have curved peripheral surfaces.

Preferably, in the trial knee joint implant, the curved peripheral surfaces form a circular cylinder shape.

Preferably, the trial knee joint implant is a trial implant for a tibia, and the trial knee joint implant is inserted in a sliding manner into a sliding groove formed in a resected surface of a proximal portion of the tibia such that the trial knee joint implant engages with the resected surface of the proximal portion of the tibia.

Preferably, in the trial knee joint implant, the articular surface of the body portion is a concavely curved surface.

Preferably, in the trial knee joint implant, the contact surface of the body portion is an inclined surface inclined by a predetermined angle.

Preferably, in the trial knee joint implant, the guide hole formed in the body portion thereof has a shape like a key hole.

According to a further aspect of the present invention, there is provided a surgical instrument for knee arthroplasty, the surgical instrument including: the trial knee joint implant; a resection guide comprising a main body including a guide portion formed to pass through the main body, the guide portion comprising a slot that guides movement of a resection device and a pin insertion hole that is formed to communicate with the slot such that a fixing pin is inserted into the pin insertion hole; and a link mechanism having a first end engaged with the guide hole of the trial knee joint implant and a second end engaged with the main body of the resection guide such that the main body of the resection guide is arranged on a medial surface or a lateral surface of a femur.

Preferably, in the surgical instrument, the pin insertion hole includes a first portion that abuts on a periphery of the slot, thereby communicating with an opening formed in the periphery of the slot, and which gradually expands such that a width thereof increases as a distance to a boundary between the first portion and the slot increases.

Preferably, in the surgical instrument, the pin insertion hole may further include a second portion that gradually constricts such that a width thereof decreases as a distance to the first portion increases.

Preferably, in the surgical instrument, the first portion and the second portion are formed to have curved surfaces.

Preferably, in the surgical instrument, the first portion and the second portion are formed to have a circular cylinder shape.

Preferably, in the surgical instrument, the slot may include a first slot vertically extending in the main body, the first slot guiding movement of the resection device to resect a distal end of a femur in a state in which the main body is arranged on a lateral surface or a medial surface of the femur; and the pin insertion hole may include a first pin insertion hole that abuts on a proximal periphery of the first slot, thereby communicating with an opening formed in the proximal periphery of the first slot.

Preferably, in the surgical instrument, the slot may further includes a second slot extending toward a posterior end of the main body from a lower end of the first slot, and the pin insertion hole may further include a second pin insertion hole that abuts on a proximal periphery of the second slot, thereby communicating with an opening formed in the proximal periphery of the second slot.

Preferably, in the surgical instrument, the link mechanism may include a height adjustment portion that adjusts a height of the main body.

According to a further aspect of the present invention, there is provided a surgical instrument for knee arthroplasty, the surgical instrument including: a spacer being inserted between a distal end of a femur and a proximal end of a tibia in a state in which a femoral component of a trial knee joint implant engages with the distal end of the femur that is resected and the proximal end of the tibia is not yet resected, the spacer having an upper surface to come into contact with the femoral component, a lower surface to come into contact with the proximal end of the tibia, and an engagement recess provided at an anterior surface thereof, an alignment handle having a first end engaged with the engagement recess of the spacer and a second end protruding from the anterior surface of the spacer; and the resection guide, wherein the alignment handle functions to position the resection guide.

Preferably, in the surgical instrument, the main body of the resection guide may further include a window formed to pass through the main body at a proximal side of the slot, and the alignment handle may be arranged to pass through the window.

According to a further aspect of the present invention, there is provided a surgical instrument for a knee arthroplasty, the surgical instrument including: a spacer inserted between a distal end of a femur and a proximal end of a tibia in a state in which a femoral component of a trial knee joint implant engages with the distal end of the femur and the proximal end of the tibia is not yet resected, the spacer having an upper surface to come into contact with the femoral component, a lower surface to come into contact with the proximal end of the tibia, and an engagement recess provided at an anterior surface of the spacer; and two horizontal alignment rods, each including an alignment portion that is a linearly elongated member and a engagement protrusion that extends perpendicularly to the alignment portion, wherein the femoral component is provided with an engagement recess at an anterior surface thereof, one of the two horizontal alignment rods is arranged such that the engagement protrusion of the horizontal alignment rod is engaged with the engagement recess of the femoral component, the other horizontal alignment rod is arranged such that the engagement protrusion of the horizontal alignment rod is engaged with the engagement recess of the spacer, and an aligned state of a knee joint is verified by checking whether the two horizontal alignment rods are parallel with each other on a coronal plane.

The embodiments of the present invention provide advantages which will be described below.

The present invention provides a resection guide enabling implantation of a knee joint implant that provides stable fixing force by having improved resistance to rotation and to external forces on the coronal plane and the sagittal plane.

The present invention provides a resection guide enabling implantation of a knee joint implant that can be loaded in a sliding manner, thereby minimizing the size of an incision, simplifying a surgical procedure, and minimizing bone loss during revision surgery.

The present invention provides a resection guide by which a drill hole formed in a bone is exposed on a resected surface of the bone to provide a sliding groove such that a knee joint implant can be loaded in a sliding manner to engage with the resected surface of the bone.

The present invention provides a resection guide having a main body that guides movement of a resection device that resects a bone, the main body being fixed to the bone by a fixing pin that has an auxiliary function of aiding guiding of the resection device.

The present invention provides a trial knee joint implant serving as a trial of a knee joint implant for arthroplasty for implanting a knee joint implant and being combined with a surgical instrument such as a resection guide during the arthroplasty, thereby simplifying a complicated surgical procedure.

The present invention provides a surgical instrument for knee arthroplasty, the surgical instrument facilitating resection of a femur and formation of a sliding groove.

The present invention provides a surgical instrument for knee arthroplasty, the surgical instrument facilitating checking of a gap between a distal end of a femur and a proximal end of a tibia and arrangement of a resection guide used for resection of the tibia.

The present invention provides a surgical instrument for knee arthroplasty, the surgical instrument facilitating checking of a gap between a femur and a tibia and alignment of the femur and tibia during a surgical operation.

The present invention provides a resection guide, a trial knee joint implant, and a surgical instrument for knee arthroplasty, all of which enable implantation of an implant having a protrusion that protrudes from a contact surface of the implant, which is to come into contact with a resected surface of a bone, wherein the protrusion engages with a sliding groove formed in the resected surface of the bone and has a portion expanded in a direction perpendicular to a direction in which the protrusion protrudes to have convex-curved surfaces, whereby the protrusion has an overall circular cylinder shape, thereby preventing concentration of stress and ensuring stable fixing force without causing damage to a bone.

The advantages or effects of the present invention are not limited to the ones described above, but other advantages or effects of the present invention can be easily anticipated from the following description by those who are skilled in the art.

DETAILED DESCRIPTION OF THE INVENTION

Figure 1:
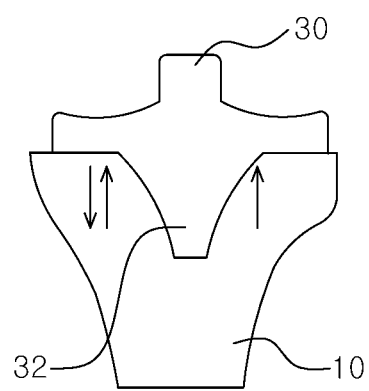
FIGS. 1 and 2 are views illustrating issues associated with an existing TKA tibial component.
Figure 2:
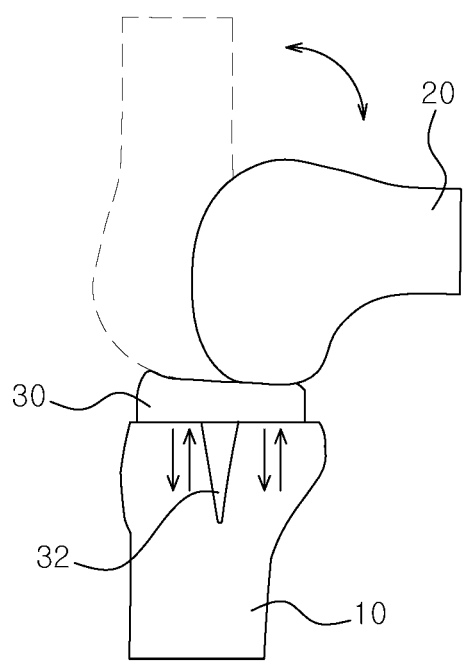
Figure 3A:
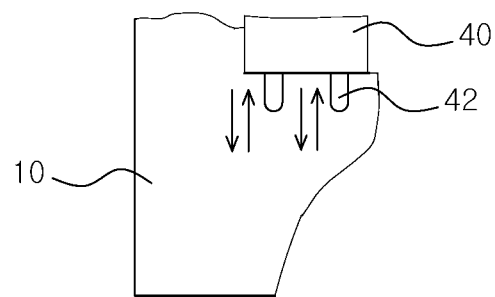
FIGS. 3A and 3B are views illustrating issues associated with an existing UKA tibial component.
Figure 3B:
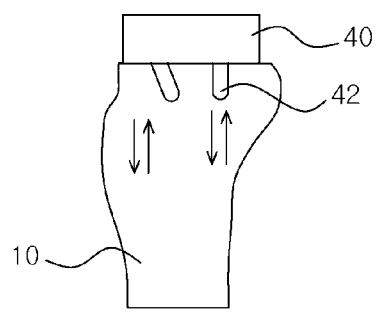
Figure 4:
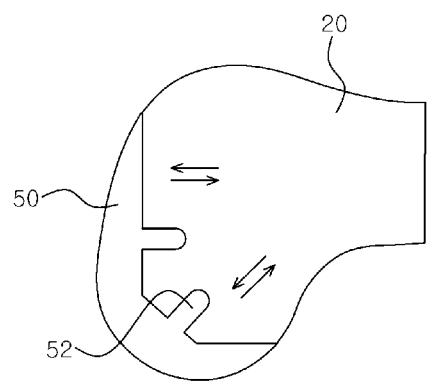
FIG. 4 is a view illustrating issues associated with an existing UKA femoral component.
Figure 5:
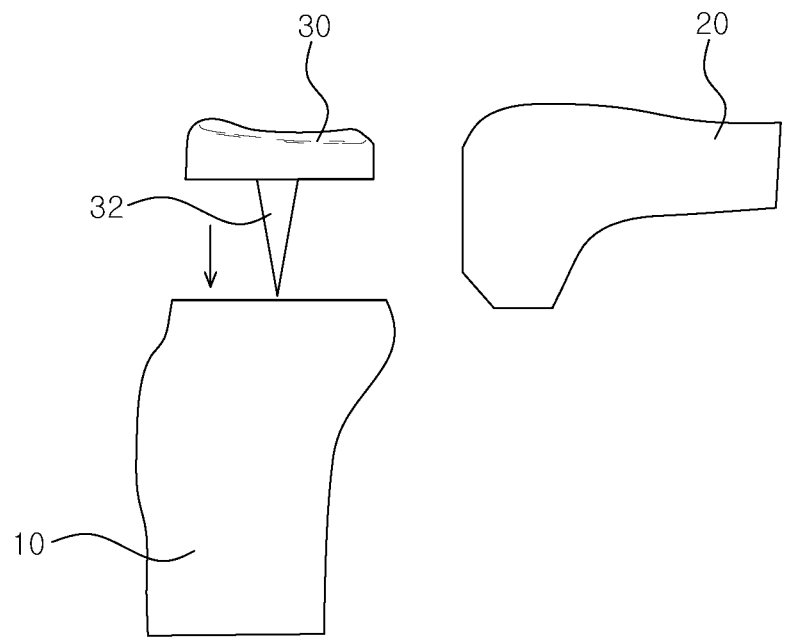
FIG. 5 is a view illustrating a top loading method of an existing TKA tibial component.
Figure 6A:
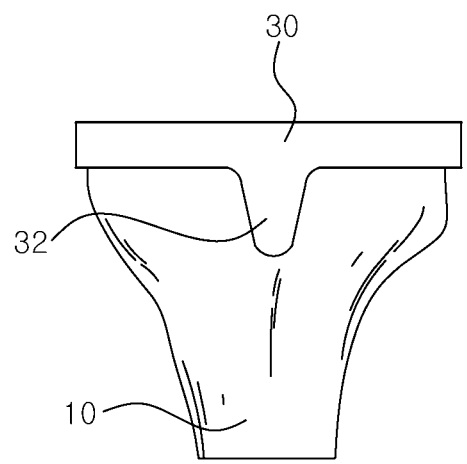
FIGS. 6A and 6B are views illustrating issues associated with an existing TKA tibial component during revision surgery.
Figure 6B:
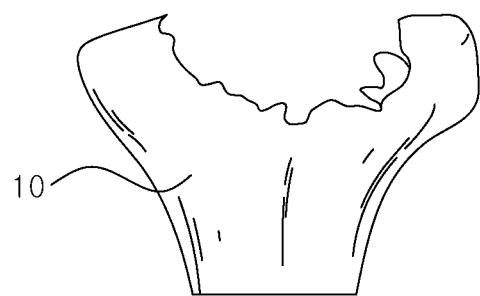
Figure 7:
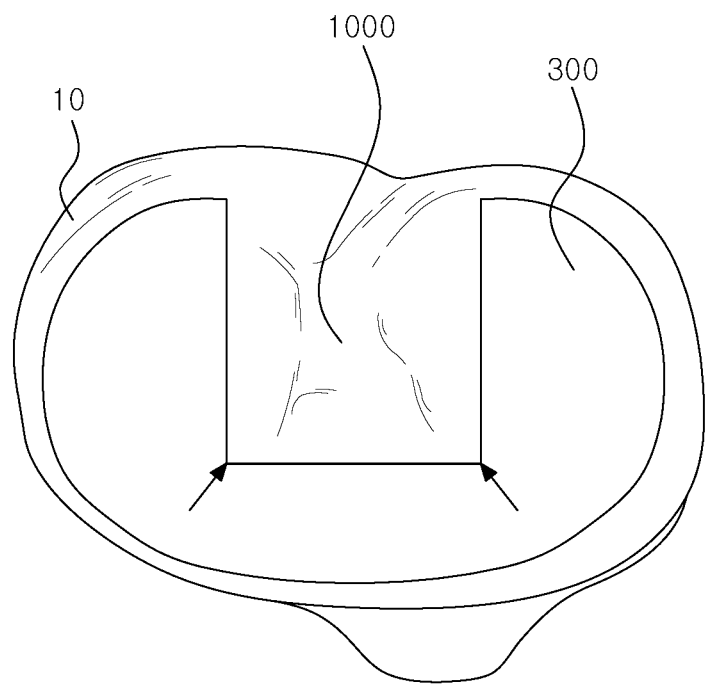
FIG. 7 is a view illustrating issues associated with an existing BCR tibial component.

Hereinbelow, a resection guide, a trial knee joint implant, and a surgical instrument for knee arthroplasty according to preferred embodiments of the present invention will be described in detail. Well-known functions or constructions will not be described in detail in case they may unnecessarily obscure the understanding of the present invention.

Specific structural and functional descriptions of embodiments of the present invention disclosed herein are only for illustrative purposes of the embodiments of the present invention. The embodiments according to the spirit and scope of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

The same reference numerals represent the same elements throughout the specification. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Below exemplary embodiments of the present invention are described in detail with reference to accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art.

Herein, the terms 'proximal' and 'distal' respectively refer to being close to and being further away from the trunk of a body. The terms 'anterior' and 'posterior' respectively refer to 'front' and 'back', and the terms 'medial' and 'lateral' respectively refer to being close to and being further away from a vertical midline that splits a body into left and right halves.

Figure 8:
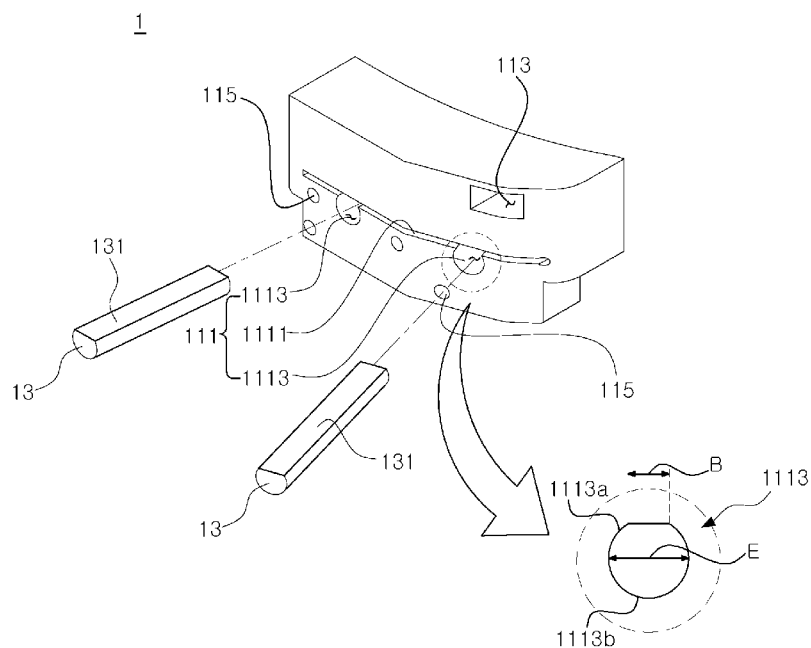
FIG. 8 is a perspective view of a resection guide according to a first embodiment of the present invention.
Figure 10A:
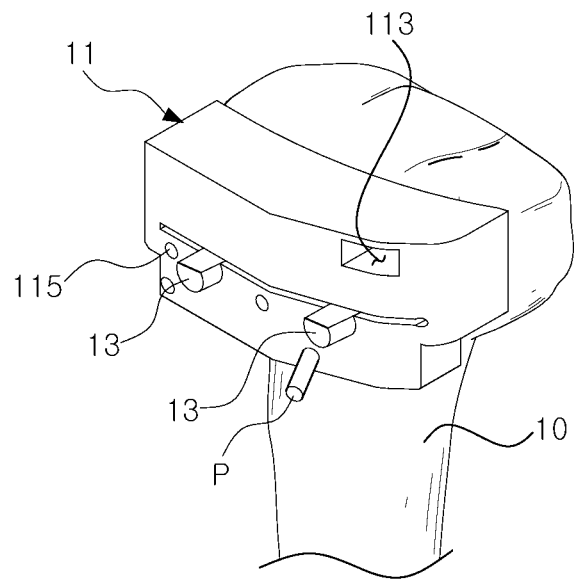
FIGS. 10A and 10B are a perspective view and a plan view illustrating a state in which the resection guide of FIG. 8 is arranged on the tibia.
Figure 10B:
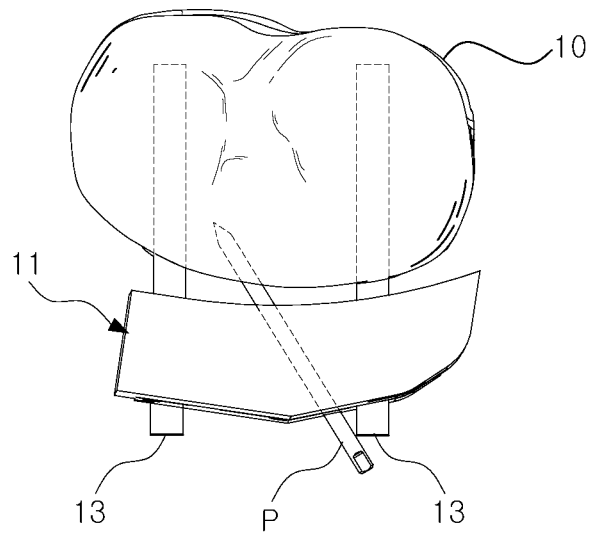

With reference to FIGS. 8, 10A and 10B, a resection guide 1 according to a first embodiment of the present invention is used for resection of a proximal end of a tibia during total knee arthroplasty (TKA). The resection guide 1 includes a main body 11 and two fixing pins 13.

The main body 11, as illustrated in FIGS. 10A and 10B, is arranged on an anterior surface of a proximal end of a tibia 10 such that the proximal end of the tibia 10 is resected by a resection device (not illustrated). The main body 11 includes a guide portion 111 formed to pass through the main body 11, a window 113, and two auxiliary pin insertion holes 115.

The guide portion 111 includes a slot 1111 that guides movement of the resection device and two pin insertion holes 1113 formed to communicate with the slot 1111 such that the fixing pins 13 can be inserted into the pin insertion holes 1113, respectively.

The slot 1111 transversely extends across the main body 11 and guides the resection device such that the resection device moves toward the medial side or the lateral side of the tibia 10, with the main body 11 arranged on the anterior surface of the tibia 10.

The pin insertion holes 1113 are formed to abut the distal side periphery of the slot 1111, thereby communicating with the slot 1111 through openings formed in the distal side periphery. Each pin insertion hole 1113 has a portion having an extended width E larger than a width B of the boundary between the slot 1111 and the pin insertion hole 113. The width of the pin insertion hole 1113 first gradually increases as it goes further away from the distal periphery of the slot and then gradually decreases as it goes further away from the distal periphery of the slot. That is, the pin insertion hole 1113 includes a first portion 1113a which is gradually expanded sideways, i.e. in a lateral-medial direction such that its width gradually increases, and a second portion 1113b which is gradually constricted such that its width gradually decreases and protrudes from the first portion 1113. The first portion 1113a and the second portion 1113b have curved peripheral surfaces. The curved peripheral surfaces form a substantially circular cylinder shape.

With reference to FIGS. 9 to 12B, after the tibia 10 is resected, the fixing pins 13 for fixing the main body 11 to the tibia are respectively inserted into drill holes H which become later sliding grooves S with which a TKA tibial component 60 is engaged later. Thus, it is possible to minimize the number of holes that need to be formed in the tibia 10 for performing arthroplasty and to simplify a surgical procedure. Accordingly, the locations and the number of the pin insertion holes 1113 are preferably determined to correspond to those of the sliding grooves S. In the resection guide 1 according to the first embodiment of the present invention, the two pin insertion holes 1113 spaced from each other are formed on the distal side of the slot 1111.

The window 113 is a through hole formed to pass through an upper portion of the main body 11 in an anterior-posterior direction. The window 113 is formed specifically at an upper portion of the guide portion 111. The window 113 allows a surgeon to see the proximal end of the tibia 10, which is screened by the main body 11. The window 113 also functions as a fixation hole into which an additional device such as an alignment device described below is inserted.

The auxiliary pin insertion holes 115 are used when it is necessary to enhance fixing force using auxiliary fixing pins P. That is, it is possible to enhance the fixing force by inserting the auxiliary fixing pins P into the auxiliary pin insertion holes 115. With reference to FIG. 10B, the auxiliary pin insertion holes 115 are obliquely formed such that the auxiliary fixing pins 6 are obliquely inserted thereinto with respect to the main body 11 for effective arrangement and fixation of the main body 11.

When the main body 11 is fixed by using additional fixing means such as auxiliary fixing pins 113 rather than the fixing pins 13, the pin insertion holes 1113 serve as drill guides for formation of the drill holes H.

The fixing pins 13 fix the main body 11 to a bone by being penetrated into the bone through the pin insertion holes 1113.

As illustrated in FIGS. 10A and 10B, each fixing pin 13 has a flat surface 131 which is arranged at a position where the pin insertion hole 1113 communicates with the slot when the fixing pin 13 is inserted through the pin insertion hole 113 to penetrate into a bone, thereby filling the opening of the periphery of the slot 1111. Since the flat surface 131 is flush with the periphery of the slot 1111, the slot 1111 can smoothly guide movement of the resection device. That is, due to the flat surface 131, the resection device, such as a saw, which moves along a longitudinal direction of the slot 1111, can be precisely and reliably perform resection of a bone.

The fixing pin 13 has a shape complementary to that of the pin insertion hole 1113. That is, the shape of the fixing pin 13 is overall cylindrical and includes a first portion having a width gradually increasing and a second portion having a width gradually decreasing.

Figure 9:
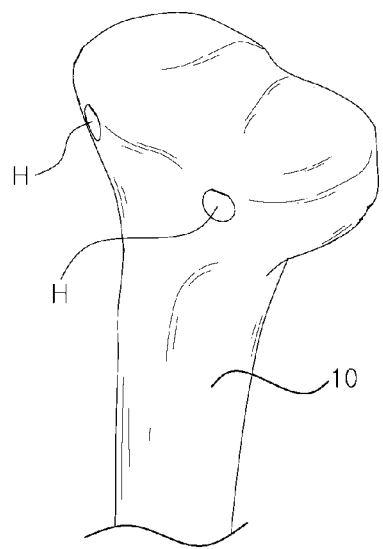
FIG. 9 is a perspective view of a tibia with a drill hole formed before arrangement of the resection guide of FIG. 8.
Figure 11:
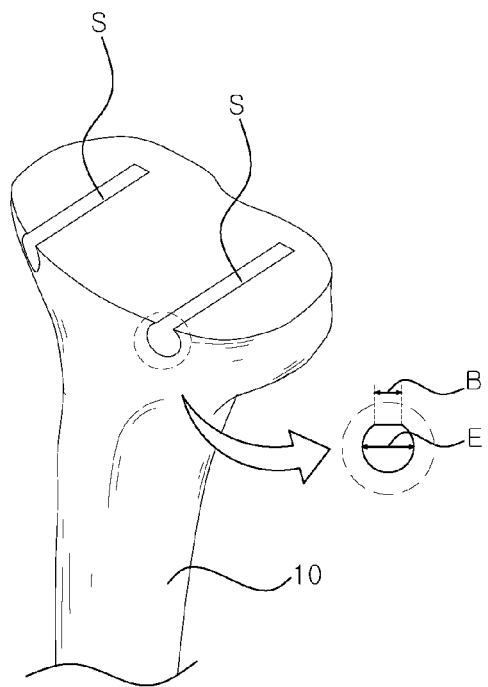
FIG. 11 is a perspective view illustrating a tibia in which a proximal portion thereof is resected while being guided by the resection guide of FIG. 8.

The resection guide 1 according to the first embodiment of the present invention, which is illustrated in FIG. 9, is placed on the anterior surface of the proximal end of the tibia 10 after the drill holes H are formed in the tibia 10 as illustrated in the FIGS. 10A and 10B. In this state, the resection device resects the tibia 10 while moving along the longitudinal direction of the slot 1111 of the resection guide 1. As a result, as illustrated in FIG. 11, the proximal end of the tibia 10 is resected, and upper parts of the drill holes H are open, thereby forming the sliding grooves S in the resected surface of the proximal end of the tibia 10. Each sliding groove S includes a portion having an extended width E larger than a width B of the opening thereof. That is, the shape of the sliding groove S is complementary to the shape of the fixing pin 13.

Figure 12A:
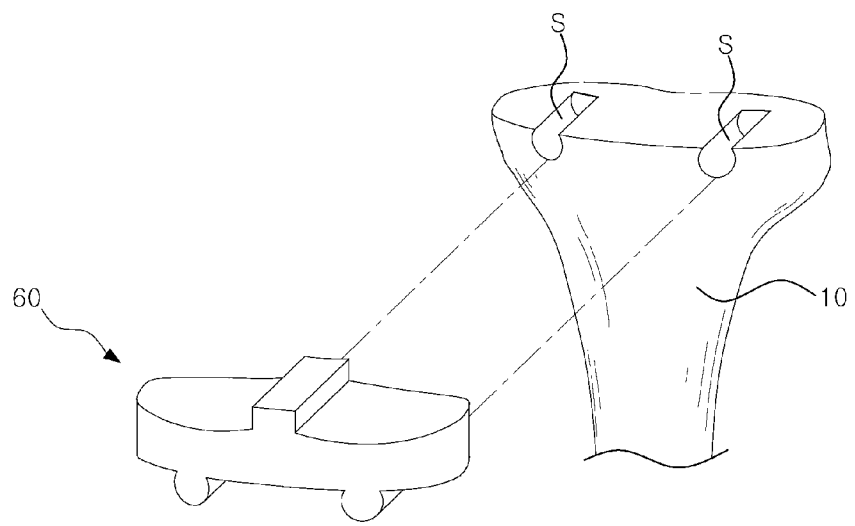
FIGS. 12A and 12B are perspective views illustrating a state in which a TKA tibial component of a knee implant is engaged with the resected surface of the proximal portion of the tibia.
Figure 12B:
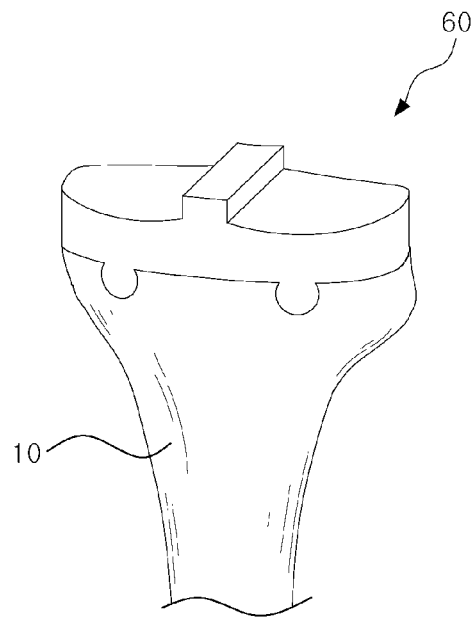
Figure 13A:
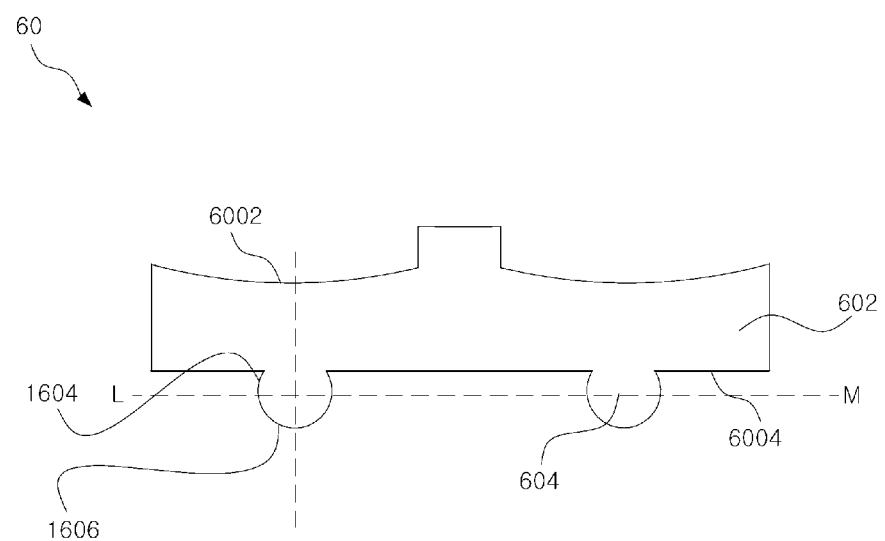
FIG. 13A to FIG. 13C are a front view, a perspective view, and a bottom view illustrating the TKA tibial component.
Figure 13B:
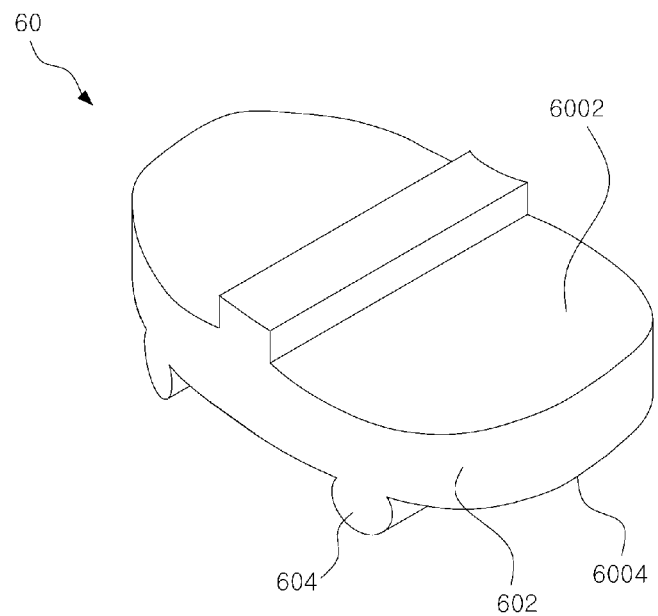
Figure 13C:
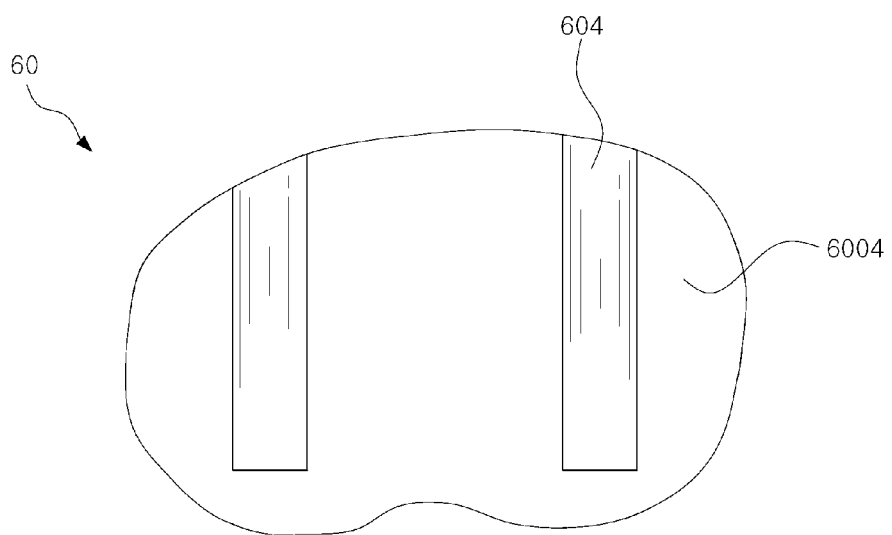

The TKA tibial component 15 is loaded on the resected surface of the tibia 10 in a manner that protrusions of the TKA tibial component 15 slide into the sliding grooves S, as illustrated in FIG. 12A and FIG. 12B. With reference to FIGS. 13A to 13C, the TKA tibial component 60 includes a body portion 602 having an articular surface 6002 and a contact surface 6004 disposed on the opposite side of the articular surface 6002. The body portion 602 serves as a substitute for the respected portion of the tibia 10 and has the articular surface 6002 to come into contact with a distal end of an overlying femur (not illustrated) such that the femur moves, on the articular surface 6002, relative to the tibia. The body portion 602 also has the contact surface 6004 to come into contact with the resected surface of the tibia 10, on the opposite side of the articular surface 6002.

The TKA tibial component 60 includes protrusions 604 that protrude downward from the contact surface 6004 and have a portion expanded sideways. The TKA tibial component 60 may have two protrusions 604.

The protrusions 604 are portions protruding from the contact surface 6004 to be fitted into the sliding grooves. The protrusions 604 have an expanded portion having a width larger than that of the other portion. The protrusion 604 has a shape corresponding to that of the pin insertion hole 1113. Preferably, the protrusion 604 protruding from the contact surface 6004 has a curved peripheral surface. As illustrated in FIG. 13A, the protrusion 604 includes a first portion 1604 protruding from the contact surface 6004 and having a traverse width gradually increasing as it goes further away from the contact surface 6004 and a second portion 1606 protruding from the first portion and having a transverse width gradually decreasing as it goes further away from the first portion 1604. Here, the transverse width means a size in a lateral-medial direction of the tibia, and the transverse width of the protrusion 604 in the lateral-medial direction increases or decreases according to positions. Therefore, the TKA tibial component 60 can be loaded in a sliding manner from the anterior side or the medial side of the tibia rather than a top loading manner.

The protrusion 604 is shaped such that its width first gradually increases as it goes further away from the surface of the body portion 602 and then gradually decreases as it goes further away from the surface of the body portion 602. For example, the protrusion 604 protruding from the contact surface 6004 may have a circular cylinder shape or an elliptic cylinder shape. That is, the cross section of the protrusion 604 may have a circular shape or an elliptical shape. However, the shape of the protrusion 604 is not limited thereto but the protrusion 604 may have any shape if the shape is composed of the first portion 1604 having a gradually increasing transverse width and the second portion 1060 protruding from the first portion 1604 and having a gradually decreasing transverse width.

The tibia 10 is provided with holes having a shape complementary to that of the protrusions 604, and the protrusions of the TKA tibial component 60 are inserted into the holes of the tibia 10 in a direction parallel to the resected surface of the tibia from the anterior side of the tibia such that the TKA tibial component 60 is engaged with the tibia 10. Since the TKA tibial component 60 is loaded in a manner of being inserted sideways rather than a conventional top-loading manner, the tibia 10 has resistance to pull-out force which is likely to be exerted on the tibial component mounted on the tibia 10. Therefore, the TKA tibial component 60 can be stably fixed to the tibia 10.

The protrusion 604 may have various shapes on the premise that the shape has an expanded portion where the width thereof increases as it goes further away from the body portion 602. As illustrated in the drawings, the protrusion 604 preferably has a circular cylinder shape. When the protrusions 604 have a triangular prism shape or a dovetail shape, forming holes having a shape complementary to that of the protrusions 604 in a bone is challenging and there is a risk of bone fracture because sharp corners of the triangular prism shape or the dovetail shape act as notches which cause stress to be concentrated on the bone. However, when the protrusions 604 have a circular cross sectional shape, there is no notch. Therefore, it is possible to prevent stress from being concentrated, thereby preventing a bone from easily breaking.

As described above, since the TKA tibial component 60 is mounted on the tibia in a manner of being inserted from the anterior side rather than in the top-loading manner and the protrusions 604 are securely fixed in the sliding grooves S due to the expanded portions of the protrusions 604, fixation of the TKA tibial component 60 to the tibia becomes easier as compared with a conventional tibial component that is mounted on the tibia in the top-loading manner, and the TKA tibial component 60 has higher resistance to the force vertically exerted on the TKA tibial component 60 due to the horizontally expanded portions of the protrusions 604.

According to the present invention, the fixing pins 13 for fixing the main body 11 of the resection guide 1 are inserted into the drill holes H formed in the tibia 10, and the drill holes H become the sliding grooves S after the proximal end of the tibia 10 is resected such that the protrusions 604 of the TKA tibial component 60 can be inserted into the sliding grooves S in a sliding manner. Therefore, it is possible to reduce the number of holes formed in the tibia 10, thereby simplifying a surgical procedure and reducing a surgery time.

Figure 14:
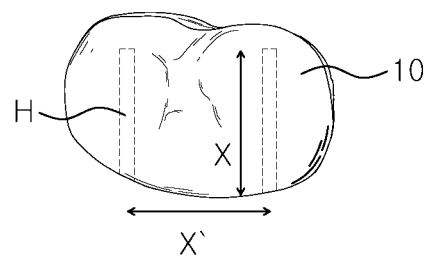
FIG. 14 is a view illustrating appropriate positions and depths of drill holes that change in accordance with the size of a tibia.
Figure 14:
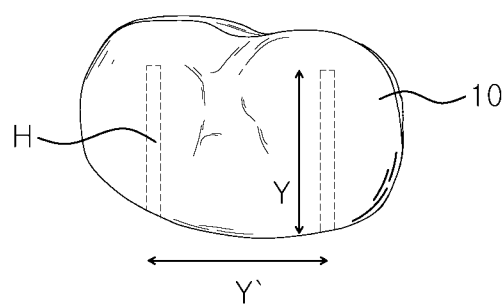
Figure 14:
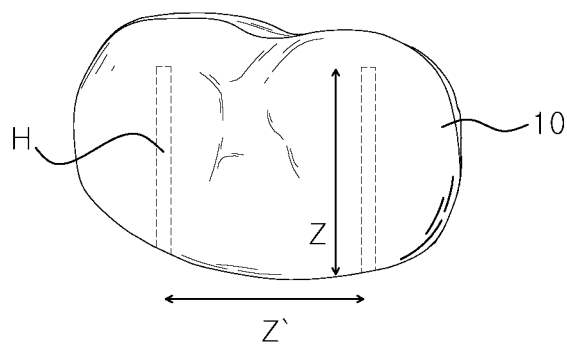

As to the drill holes H formed in the tibia 10 illustrated in FIG. 9, the locations and depths of the drill holes H vary depending on the size of the tibia 10 as illustrated in FIG. 14. That is, the distance between the drill holes H and the depth of the drill holes H increase as the size of the tibia 10 increases. Therefore, preferably, a drill guide 2 illustrated in FIG. 15 is used when forming the drill holes H in the tibia 10.

Figure 15:
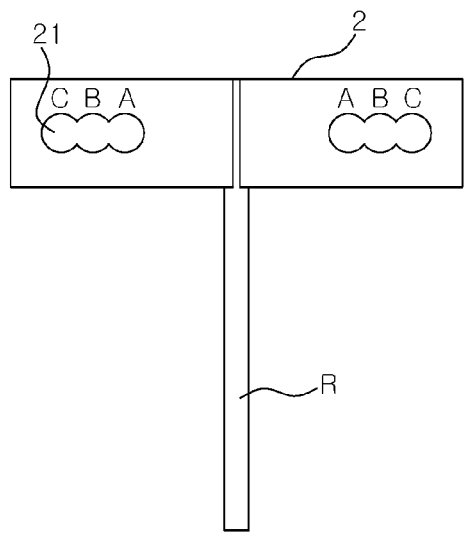
FIG. 15 is a front view illustrating a drill guide according to one embodiment of the present invention.

With reference to FIG. 15, the drill guide 2 includes two sets of drill guide holes 21 arranged in a horizontal direction. The two sets of the drill guide holes 21 are symmetrically arranged with respect to a midline of the drill guide 2. That is, each of the left side and the right side of the drill guide 2 is provided with three drill guide holes 21. The drill guide holes 21 arranged from a middle portion to a periphery portion of the drill guide are respectively denoted by letters A, B, and C. The drill guide holes A, B, C have an equal diameter but indicate drill holes having different depths. That is, the drill guide hole 21 that is closer to the periphery of the drill guide 2 indicates a drill hole having a deeper depth. With reference to FIGS. 14 and 15, the drill guide holes denoted by the letter A are holes used to form drill holes H having a depth X and being distanced from each other by a length X' in a tibia 10 having a small size, the drill guide holes denoted by the letter B are holes used to form drill holes H having a depth Y and being distanced from each other by a length Y' in a tibia 10 having a middle size, and the drill guide holes denoted by the letter C are holes used to form drill holes H having a depth Z and being distanced from each other by a length Z' in a tibia 10 having a large size (Z>Y>X, Z'>Y'>X').

As a drilling device, a plurality of drill bits (not illustrated) of different lengths corresponding to the depths of drill holes may be prepared, or one drill bit marked with lines corresponding to the depths of the drill guide holes A, B, and C is prepared.

A rod R may be attached to the drill guide 2. The rod R may be an EM rod.

Figure 16:
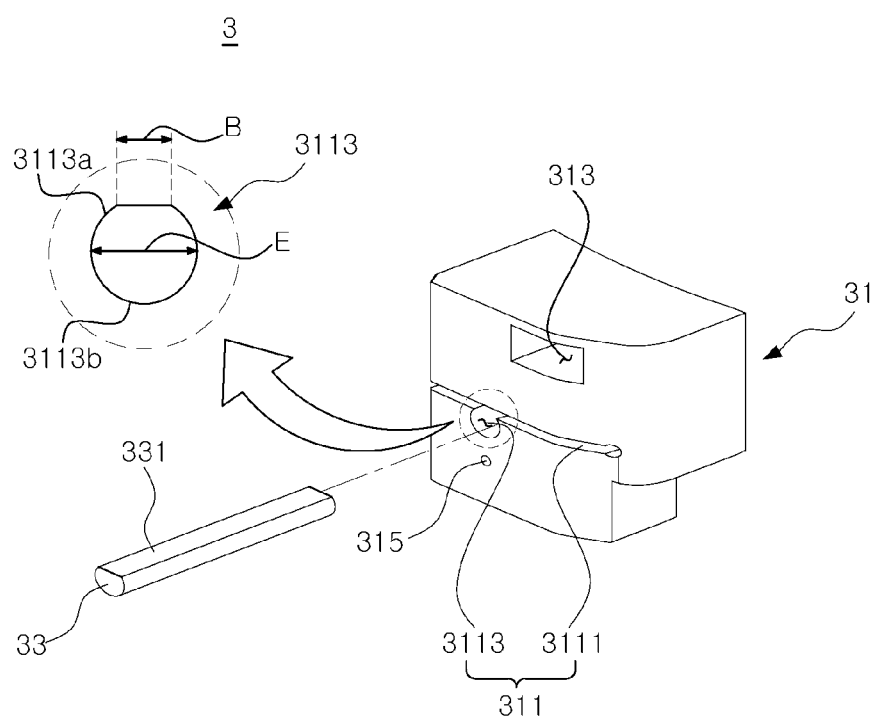
FIG. 16 is a perspective view illustrating a resection guide according to a second embodiment of the present invention.
Figure 17:
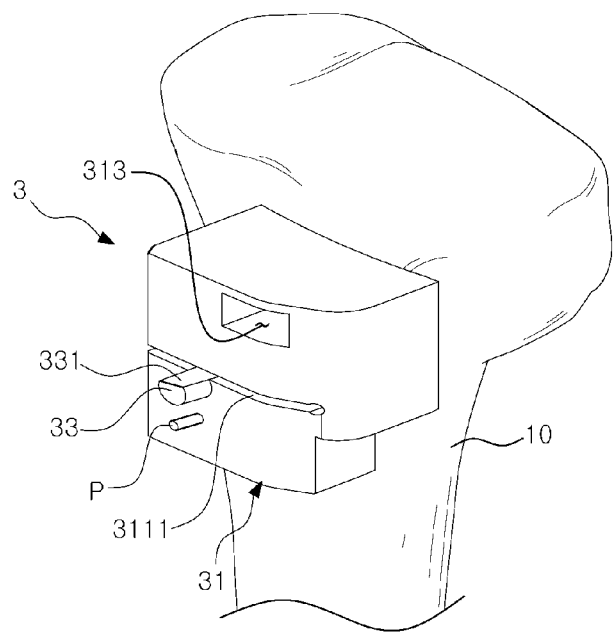
FIG. 17 is a perspective view illustrating a state in which the resection guide of FIG. 16 is arranged on a tibia.

With reference to FIGS. 16 and 17, a resection guide 3 according to a second embodiment of the present invention will be described. The resection guide 3 is used to guide resection of a proximal end of a tibia during unicompartmental knee arthroplasty (UKA). The resection guide 3 includes a main body 31 and a fixing pin 33.

The main body 31 is a component to be arranged on the anterior surface of a proximal end of a tibia 10 to guide a resection device (not illustrates) that resects the proximal end of the tibia 10. The main body 31 includes a guide portion 311 formed to pass through the main body 31, a window 313, and an auxiliary pin insertion hole 315.

The guide portion 311 includes a slot 4111 that guides movement of the resection device and a pin insertion hole 311 that is formed to communicate with the slot 3111 and into which the fixing pin 33 is inserted.

The slot 3111 extends in a medial-lateral direction, and an end of the slot 3111 in a direction along which the resection device is guided is open. The pin insertion hole 3113 is formed on a distal side of the slot 3111, and has an expanded portion having a width E that is larger than a width B of the boundary between the slot 3111 and the pin insertion hole 3113.

The pin insertion hole 3113 is shaped such that its width first increases as it goes further away from the slot and then decreases as it goes further away from the slot. That is, the pin insertion hole 3113 includes a first portion 3113a that is gradually expanded sideways, i.e. in a lateral-medial direction, and a second portion 3113b that protrudes from the first portion 3113a and is gradually constricted sideways. The first portion 3113a and the second portion 3113b have curved peripheral surfaces, and the curved peripheral surfaces form a circular cylinder shape.

With reference to FIGS. 16 to 20B, after the proximal end of the tibia 10 is resected, the fixing pin 33 for fixing the main body 31 is inserted into a drill hole H that is formed in the tibia 10 and which is changed into a sliding groove S later into which a UKA tibial component 70 is fitted after the tibia 10 is resected. Therefore, it is possible to minimize the number of holes that need to be formed in the tibia 10 and to simplify a surgical procedure. The number and the location of the pin insertion hole 3113 vary depending on the number and the location of the sliding groove S. In the resection guide 3 according to the second embodiment, the pin insertion hole 3113 is formed on the distal side of the slot 3111 and only one pin insertion hole 3113 is provided.

The window 313 is a through hole formed to pass through an upper portion of the guide portion 311 of the main body 31. As described above, the window 313 allows a surgeon to see the tibia 10 therethrough or serves as a fixing hole into which an additional device is inserted.

The auxiliary pin insertion hole 315 is a through hole into which an auxiliary fixing pin P is inserted to increase the force of fixing the resection guide. With reference to FIG. 17, the auxiliary pin insertion hole 315 is an oblique hole such that the auxiliary fixing pin P is inserted obliquely with respect to the lateral direction for effective arrangement and fixation of the main body 31.

The fixing pin 33 has a complementary shape to the pin insertion hole 3113 and is an elongated member to be inserted into the pin insertion hole 3113. The fixing pin 33 partially has a flat surface 331 to smoothly guide movement of the resection device. The function and the shape of the fixing pin 33 are similar to those of the fixing pin 13 of the resection guide 1 according to the first embodiment.

The resection guide 3 according to the second embodiment of the present invention guides resection of the tibia 10 during a unicompartmental knee arthroplasty (UKA). Although the resection guide 3 differs from the resection guide 1 in the shape thereof and the number of the pin insertion holes 3113, the functions and roles of the parts of the resection guide 3 are the same as those of the resection guide 1. Therefore, a detailed description about the functions and roles of each part of the resection guide 3 will be omitted.

Figure 18:
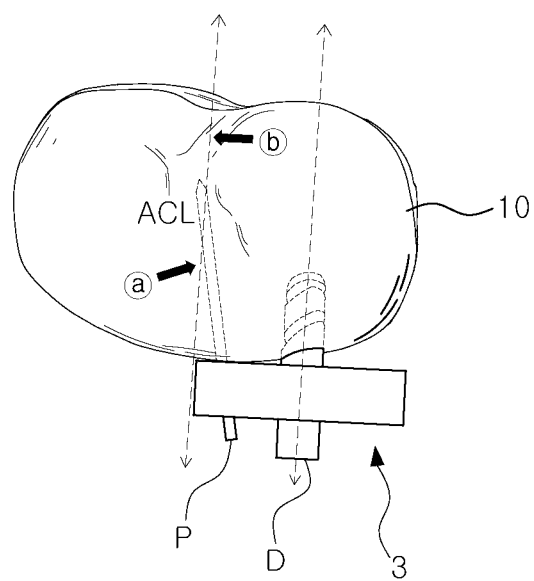
FIG. 18 is a plan view illustrating a process of drilling a drill hole using the resection guide of FIG. 16.

FIG. 18 illustrates a process of forming a drill hole H in the tibia 10 before resecting the proximal end of the tibia 10 using the resection guide 3 of FIG. 16. FIG. 18 is a schematic view illustrating a state in which drilling a drill hole with a drill bit D is guided by the pin insertion hole 3113 of the resection guide 3 according to the second embodiment of the present invention. The drill hole H finally becomes the sliding groove S used to combine an implant with the tibia 10. Therefore, proper guiding needs to be performed before the drill hole H is formed. This is because the tibial component can be arranged with an accurate orientation only when accurate alignment is achieved. Specifically, correct resection landmarks are posteriorly a lateral edge (point b) of a medial femoral condyle and anteriorly a medial edge (point a) of a anterior tibial spine with which an anterior cruciate ligament (ACL) is in contact.

Figure 19:
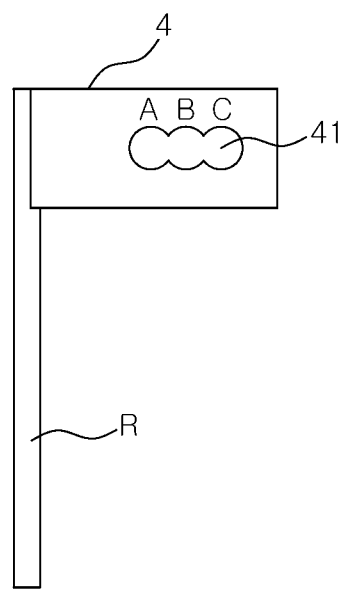
FIG. 19 is a front view illustrating a drill guide according to the second embodiment of the present invention.

When forming a drill hole H in the proximal end of the tibia 10 for UKA, a drill guide 4 illustrated in FIG. 19 can be used instead of the resection guide 3 according to the second embodiment of the present invention. The location and the depth of the drill hole H vary depending on the size of the tibia 10 as illustrated in 14, wherein only either left or right side rather than both the left and right sides is considered in UKA. Accordingly, the drill guide 4 of FIG. 18 includes drill guide holes 41 arranged to be continuous to each other in a horizontal direction. Specifically, the drill guide holes 41 are respectively denoted by letters A, B, and C in the order from the medial side to the lateral side. As described above, the drill guide holes 41 have an equal size but indicate drill holes having different depths, respectively. The drill guide hole that is closer to the lateral side indicates a drill hole having a deeper depth. As a drill bit mounted to a drilling device, a plurality of drill bits having various lengths respectively corresponding to the depths of the drill holes indicated by the drill guide holes 41 is prepared, or one drill bit marked with marks corresponding to the depths of the drill holes indicated by the drill guide holes A, B, and C is prepared. The drill guide 4 is combined with a rod R, and the rod R may be an EM rod.

Figure 20A:
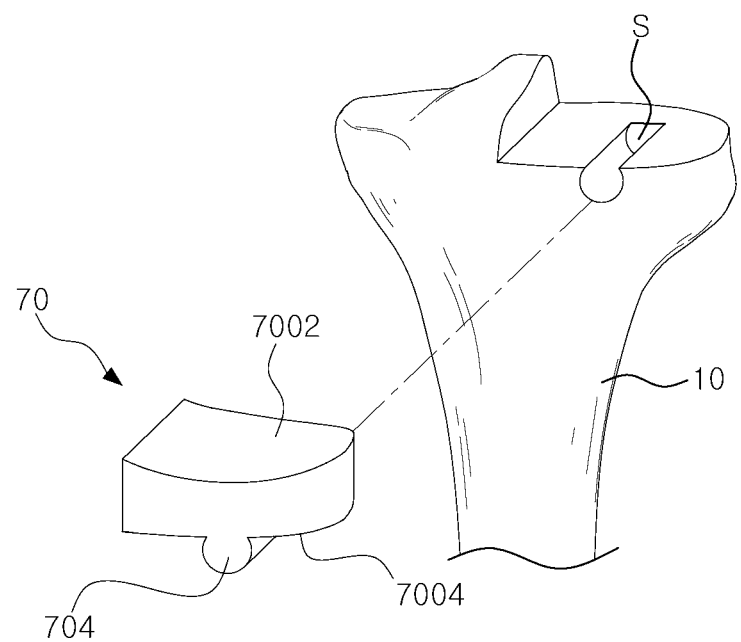
FIGS. 20A and 20B are perspective views illustrating a state in which a UKA tibial component of a knee joint implant is arranged on the resected surface of a proximal end of a tibia.
Figure 20B:
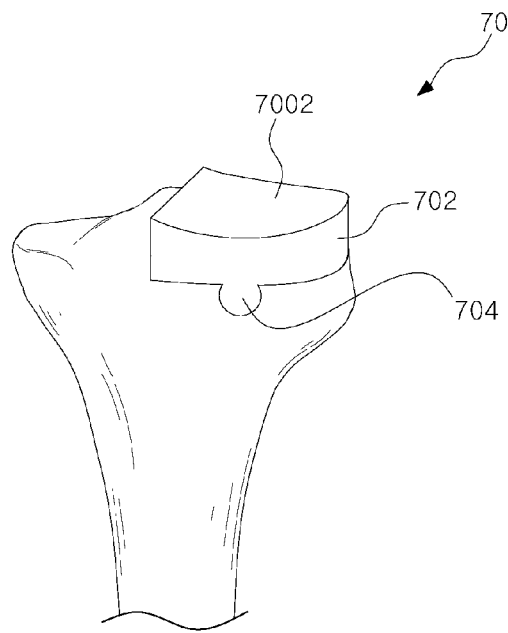

FIG. 20A illustrates a state in which the resected surface having the sliding groove S is formed at the proximal end of the tibia 10 by using the resection guide 3 according to the second embodiment of the present invention, and also illustrates a knee joint implant, i.e. a UKA tibial component 70 to be engaged with the sliding groove S. FIG. 20B illustrates a state in which the UKA tibial component 70 is engaged with the tibia 10.

The UKA tibial component 70 includes a body portion 702 having an articular surface 7002 and a contact surface 7004 disposed on the opposite side of the articular surface 7002. The body portion 720 is a substitute for the resected portion of the tibia 10, and the articular surface 7002 is a surface to come into contact with an overlying femur. The contact surface 7004 is disposed on the opposite side of the articular surface 7002 and comes into contact with the resected surface of the tibia 10.

The UKA tibial component 70 includes a protrusion 704 protruding from the contact surface 7004 and having an expanded portion that is expanded sideways. The UKA tibial component is preferably provided with one protrusion 704. The protrusion 704 is a portion protruding from the contact surface 7004 and being fitted into a groove formed in a resected surface of a bone. The protrusion 704 has an expanded portion that is complementary to the shape of the pin insertion hole 3113.

Figure 21:
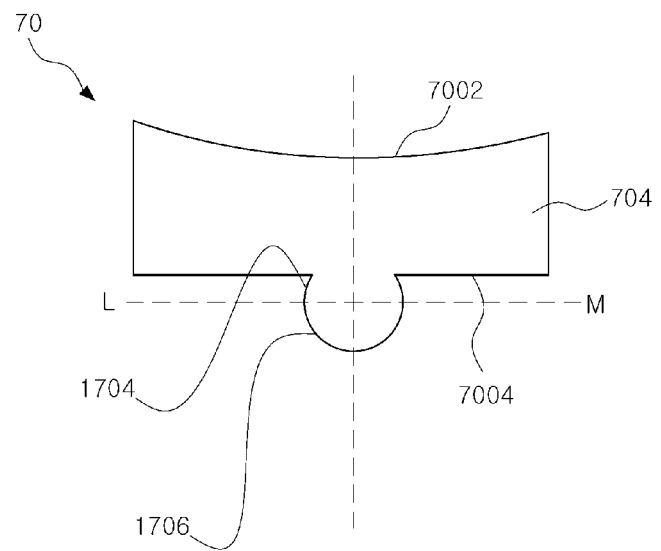
FIG. 21 is a front view of the UKA tibial component.

The features of the protrusion 704 of the UKA tibial component 70 are similar to those of the protrusion 604 of the TKA tibial component 60 described above. That is, as illustrated in FIG. 21, preferably, the protrusion 704 includes a first portion 1704 protruding from the contact surface 7004 and being gradually expanded sideways and a second portion 1706 protruding from the first portion 1704 and being gradually constricted sideways. The term 'sideways' refers to a lateral-medial (L-M) direction of the tibia. The width of the protrusion 704 in the lateral-medial direction may vary according to positions. Therefore, the UKA tibial component 70 can be inserted from the anterior side in a sliding manner rather than a top-loading manner. Therefore, stable fixation can be achieved.

As described above, according to the present invention, the fixing pin 33 for fixing the main body 31 of the resection guide 3 is inserted into the drill hole H formed in the tibia 10. In addition, after the resection of the tibia 10, the drill hole H becomes the sliding groove S and the protrusion 704 of the UKA tibial component 70 is inserted into the sliding groove S in a sliding manner. Therefore, it is possible to minimize the number of holes that need to be formed in the tibia 10, simplify a surgical procedure, and reduce a surgery time.

Figure 22:
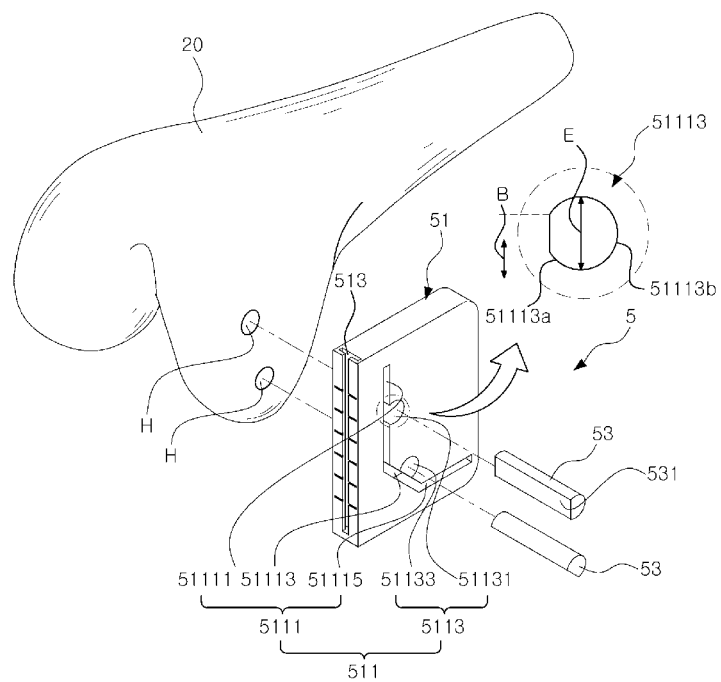
FIG. 22 is a perspective view of a resection guide according to a third embodiment of the present invention.

With reference to FIG. 22, a resection guide 5 according to a third embodiment of the present invention will be described. The resection guide 5 is used to guide resection of a distal end of a femur during UKA or TKA surgery, and includes a main body 51 and a fixing pin 53.

The main body 51 is arranged on the lateral surface or the medial surface of the distal end of the femur 20 such that the distal end of the femur 20 is resected by a resection device (not illustrated). The main body 51 includes a guide portion 511 formed to pass through the main body 51.

The guide portion 511 includes a slot 5111 that guides movement of the resection device and a pin insertion hole 5113 that is formed to communicate with the slot 5111 and into which a fixing pin 51 is inserted.

The slot 5111 includes a first slot 51111 vertically extending across the main body 51, a second slot 51113 extending toward a posterior side of the main body 51 from a lower end of the first slot 51111, and a third slot 51115 extending toward a proximal side from an posterior end of the second slot 51113, thereby guiding movement of the resection device to resect the distal end of the femur 20 in a state in which the main body 51 is arranged on the lateral surface or the medial surface of the femur 20. The second slot 51113 obliquely extends toward the posterior side of the main body from the lower end of the first slot 51111. The slot 5111 may include an additional slot besides the first to third slots 51111 to 51115 to additionally resect an anterior portion of the distal end of the femur 20.

The pin insertion hole 5113 includes a first pin insertion hole 51131 formed on a proximal side of the first slot 51111 such that the periphery of the first pin insertion hole 51131 partially abuts on a proximal-side periphery of the first slot 51111. The first pin insertion hole 51131 is shaped such that the width thereof first increases as it goes further away from the first slot 51111 and then decreases as it goes further away from the first slot 51111. That is, the first pin insertion hole 51131 includes a first portion 51113*a* having a width that gradually increases and a second portion 51113*b* having a width that gradually decreases. The first portion 51113*a* and the second portion 51113*b* have curved peripheral surfaces, and the curved peripheral surfaces form a circular cylinder shape. The second pin insertion hole 51133 may have the same shape as the first pin insertion hole 51131.

Figure 23A:
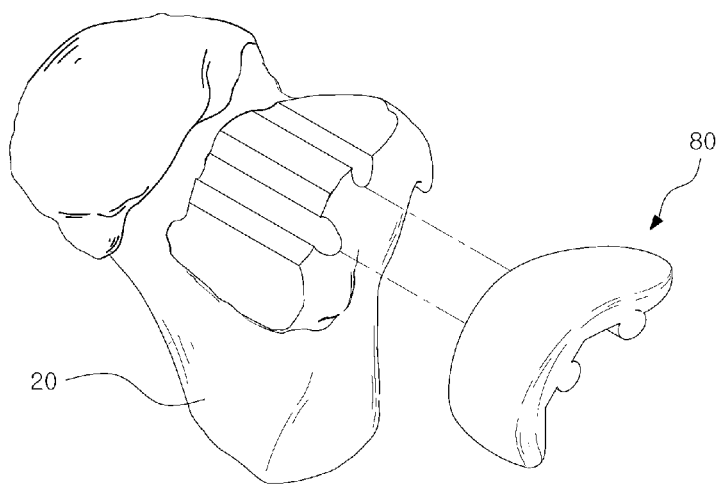
FIGS. 23A and 23B are perspective views illustrating a state in which a UKA femoral component of a knee joint implant is arranged on the resected surface of a distal end of a femur.
Figure 23B:
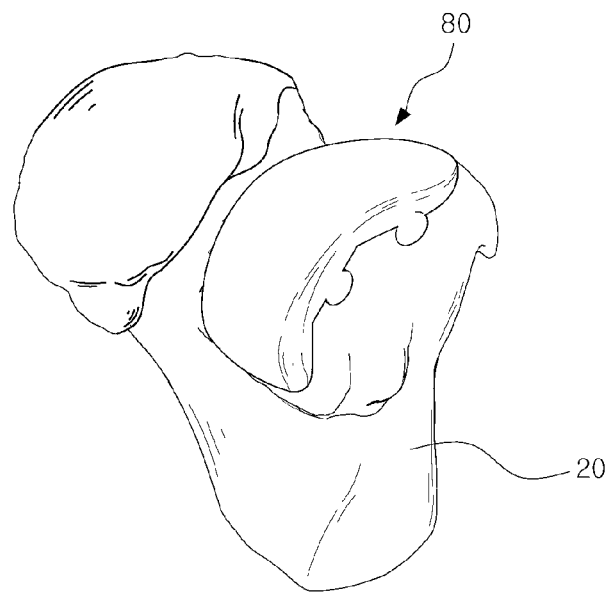

With reference to FIGS. 22 to 23B, the fixing pin 53 for fixing the main body 51 is inserted into a drill hole H that becomes a sliding groove S later into which a UKA femoral component 80 is fitted after the femur 20 is resected. Therefore, it is possible to minimize the number of holes that need to be formed in the femur 20 for an arthroplasty surgery and to simplify a surgical procedure. Accordingly, the locations and the number of the pin insertion holes 5113 are determined to correspond to those of the sliding grooves S. In the resection guide 5 according to the third embodiment of the present invention, as the pin insertion hole 5113, there are two pin insertion holes 5113 that are respectively disposed on proximal sides of the first slot 51111 and the second slot 51113.

An anterior surface of the main body 51 is provided with a slit-like recess 513 that extends in a vertical direction, and the slit-like recess 513 is engaged with a link mechanism for fixing the resection guide 5 as described below.

The fixing pin 53 has a shape complementary to that of the pin insertion hole 5113. The fixing pin 53 is penetrated into the femur through the pin insertion hole 1113, thereby fixing the main body 51. The fixing pin 53 partially has a flat surface 531 to form a planar resected surface of a bone.

Drill holes H are formed on the medial side or the lateral side of the femur 20 such that the fixing pins 53 are inserted into the drill holes H. The resection guide 5 according to the third embodiment is attached to the medial side or the lateral side of the femur 20 by an additional device as described below. In this case, the pin insertion holes 5113 also function as guides for guiding drilling of the drill holes H. That is, both the formation of the drill holes H and the resection of the femur can be performed with the resection guide 5. Therefore, it is possible to simplify a surgical procedure and reduce a surgery time.

The resection guide 5 according to the third embodiment of the present invention may further include an auxiliary pin insertion hole into which an auxiliary fixing pin is inserted as necessary.

When the femur 20 is resected using the resection guide 5 according to the third embodiment of the present invention, as illustrated in FIG. 23A, the resected surface with sliding grooves S is formed at the distal end of the femur 20 for UKA surgery. Accordingly, as illustrated in FIG. 23B, a UKA femoral component 80 can be inserted from the medial side or the lateral side of the femur 20 in a sliding manner such that the UKA femoral component 80 is engaged with the femur 20. In addition, the resected surface of the femur 20 for TKA surgery also can be formed by using the resection guide 5 according to the third embodiment of the present invention. In this case, the resected surface of the femur 20 is provided with sliding grooves S so that a TKA femoral component (not illustrated) can be engaged with the femur.

Figure 24A:
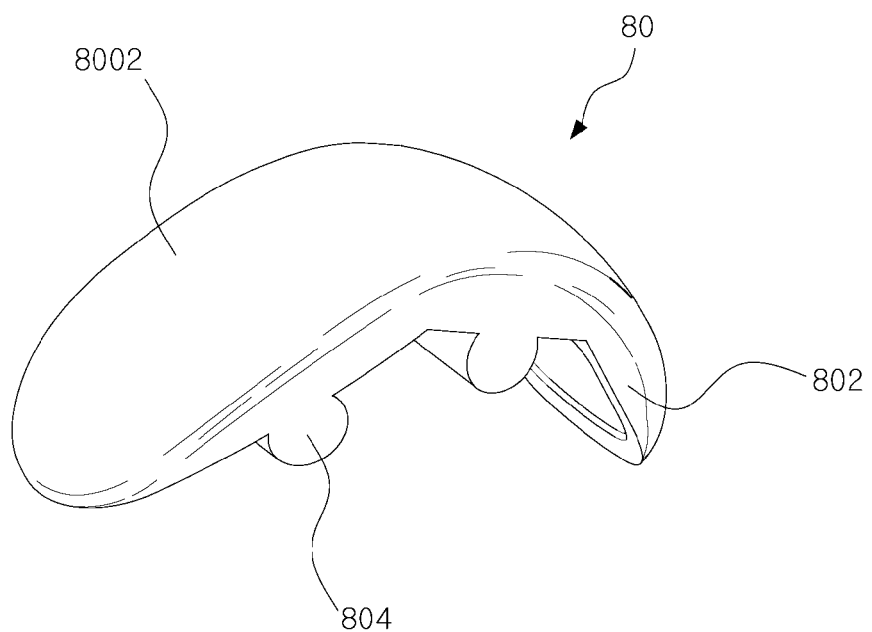
FIG. 24A to FIG. 24C are a top perspective view, a bottom perspective view, and a side elevation view illustrating a UKA femoral component.
Figure 24B:
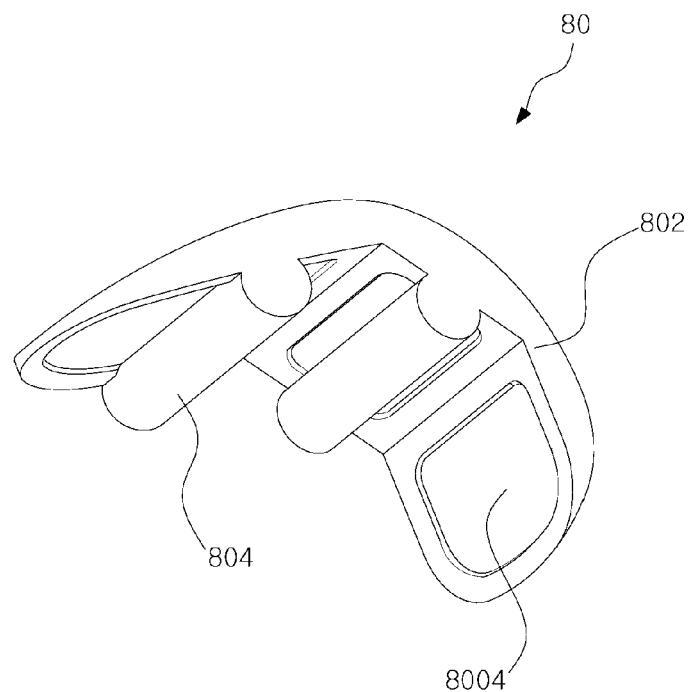
Figure 24C:
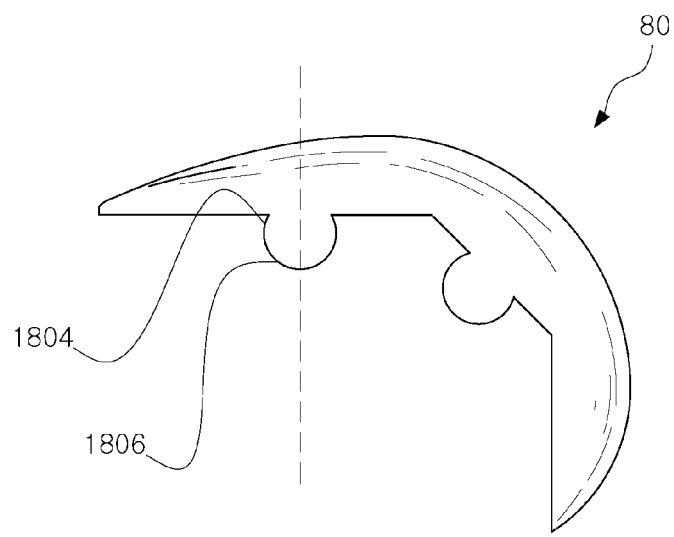

With reference to FIGS. 24A to 24C, the UKA femoral component includes a body portion 802 having an articular surface 8002 and a contact surface 8004 disposed on the opposite side of the articular surface 8002. The body portion 802 is a substitute for the resected portion of the femur 20. The articular surface 8002 comes into contact with the underlying tibia (not illustrated) and serves as a surface on which the tibial component moves relative to the femur. The opposite side of the articular surface 8002 serves as the contact surface 8004 that comes into contact with the femur 20.

The UKA femoral component 80 includes protrusions 804 protruding from the contact surface 8004 and having portions expanded sideways. Preferably, the femoral component has at least two protrusions.

The protrusions 804 are portions protruding from the contact surface 8004 to be fitted into grooves formed in the resected surface of a bone. The protrusions 804 have portions expanded sideways. Preferably, the peripheral surfaces of the protrusions 804 protruding from the contact surface 8004 are curved. Preferably, each protrusion 804 includes a first portion 1804 protruding from the contact surface 8004 and being gradually expanded sideways such that the width thereof increases with increasing distance to the contact surface 8004 and a second portion 1806 protruding from the first portion 1804 and being gradually constricted sideways such that the width thereof decreases with increasing distance to the first portion 1804. The term 'sideways' means a direction perpendicular to a direction in which the protrusions 804 protrude from the contact surface 8004.

As illustrated in the drawings, the protrusions 804 are shaped such that the width thereof first increases as it goes further away from the body portion 802 and then decreases as it goes further away from the body portion 802. For example, the protrusions 804 may have a circular cylinder shape or a elliptical cylinder shape protruding from the contact surface 8004. That is, the cross section of the protrusion 804 has a circular shape or an elliptical shape. However, the cross sectional shape of the protrusion 804 is not limited to a circle or an eclipse but may be any shape if the shape is composed of the first portion 1804 that is gradually expanded sideways and the second portion 1806 that protrudes from the first portion 1804 and is gradually constricted sideways.

The femur is provided with holes having a shape complementary to that of the protrusions 804, and the UKA femoral component 80 according to the present invention is inserted from the lateral side or the medial side that is perpendicular to a direction of the superior side such that the UKA femoral component 80 is attached to the femur. Accordingly, in the case of the UKA femoral component 80 according to the present invention, the femoral component 80 is inserted from the lateral side or the medial side rather than being inserted in a direction parallel to a longitudinal direction of the femur. Therefore, the UKA femoral component 80 has resistance to pull-out force that is likely to be exerted on the femoral component attached to the femur, thereby providing stable fixing force.

The protrusions 804 may have various shapes on the premise that the shape have a portion having a width that increases as it goes further away from the body portion 802. As illustrated in the drawings, preferably, the protrusions 804 have a circular cylinder shape. When the protrusions 804 have a triangular prism shape or a dovetail shape, forming fixation holes having a shape complementary to that of the protrusions 804 in a bone by partially removing the bone is challenging and there is a high risk that a bone fracture occurs because sharp corners of the triangular prism shape or the dovetail shape act as notches which cause stress to be concentrated on the bone. However, according to the present invention, since the protrusions do not have notches by having a round shape such as a circular cross section, stress is not concentrated, thereby preventing bone fracture.

In addition, since a middle portion of the protrusion 804 in the vertical direction is expanded sideways to have a larger width than upper and lower end portions of the protrusion 804, the protrusion 804 provides stable fixing force with respect to the femur 20. As illustrated in FIG. 23A, the UKA femoral component 80 is attached to the femur 20 in a manner of being inserted in a sliding manner from the lateral side or the medial side of the femur. That is, the UKA femoral component 80 is inserted in a direction parallel to the horizontal surface of the femur 20. Therefore, the protrusions 804 provide high resistance to pull-out force that is vertically exerted, thereby providing fixing force to resist the force vertically exerted on the knee joint and stable resistance enough to resist rocking force. Furthermore, even when a rocking motion occurs during rolling back, the protrusions 804 can maintain stable fixation of the femoral component 80. In addition, according to the present invention, since the UKA femoral component 80 is inserted from the lateral side or the medial side of the femur, it is possible to reduce the size of an incision and simplify a surgical procedure.

According to the present invention, the fixing pins 53 for fixing the main body 51 of the resection guide 5 to the femur 20 are inserted into the drill holes H formed in the femur 20, the drill holes H are changed into the sliding grooves S after the femur is resected, and the protrusions 804 of the UKA femoral component 80 are fitted into the sliding grooves S of the femur 20. Therefore, it is possible to minimize the number of holes that need to be formed in the femur, simplify a surgical procedure, and reduce a surgery time.

Figure 25:
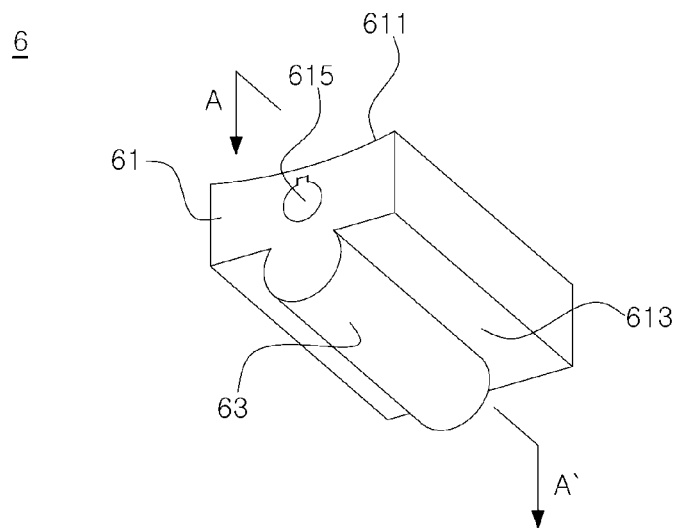
FIG. 25 is a perspective view illustrating a trial knee joint implant according to one embodiment of the present invention.
Figure 26A:
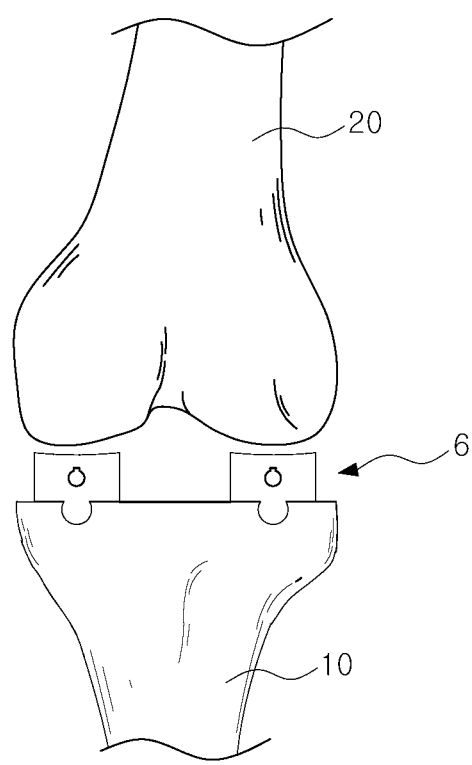
FIG. 26A to FIG. 26C are views showing use examples of the trial knee joint implant respectively during TKA, UKA and BCR.
Figure 26B:
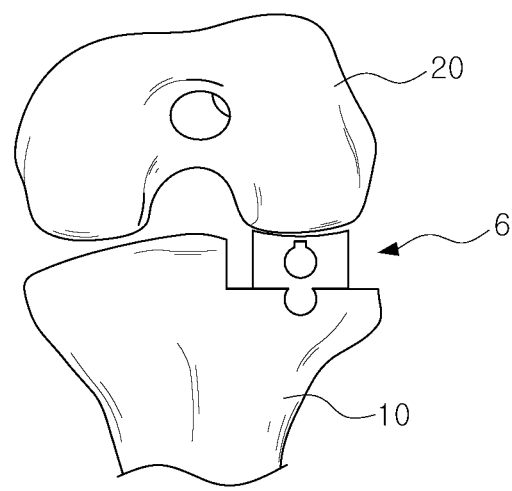
Figure 26C:
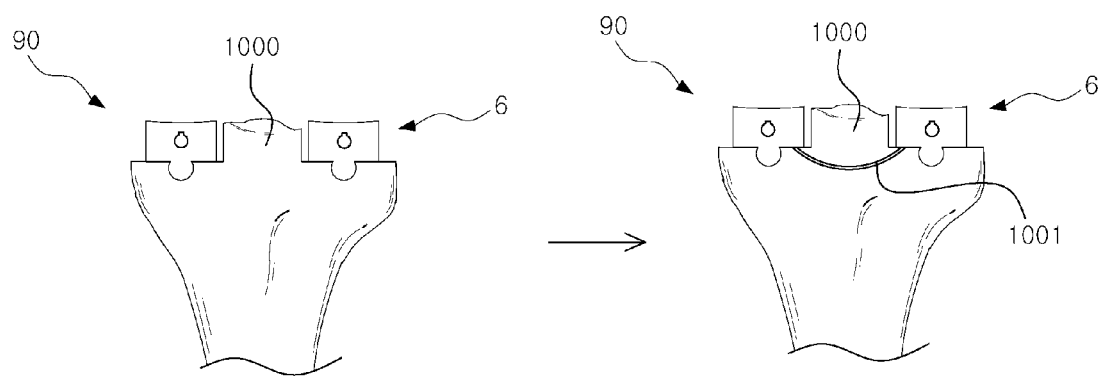

With reference to FIG. 25, a trial knee joint implant 6 according to a first embodiment will be described. The trial knee joint implant 6 is a trial tibial component, and includes a body portion 61 and a protrusion 63. As illustrated in FIGS. 26A to 26C, the trial knee joint implant 6 is slidingly engaged with the sliding grooves formed in the resected surface of the proximal end of the tibia 10, and the trial knee joint implant 6 is used to check for knee kinematics before resecting the femur 20 or to properly arrange or fix a surgical instrument such as a resection guide in place.

The body portion 61 is engaged with the sliding grooves formed in the resected surface of the proximal end of the tibia and includes an articular surface 611, a contact surface 613, and a guide hole 615. The thickness of the body portion 61 varies according to the size of a real knee joint implant.

As illustrated in FIGS. 26A and 26B, the articular surface 611 is a concavely curved surface. The reason that the articular surface 611 is concavely curved is that it is a portion to be in contact with the distal end of the femur 20 before the distal end of the femur 20 is resected and the concavely curved surface facilitates checking for extension, flexion, and mid-range stability.

Figure 27A:
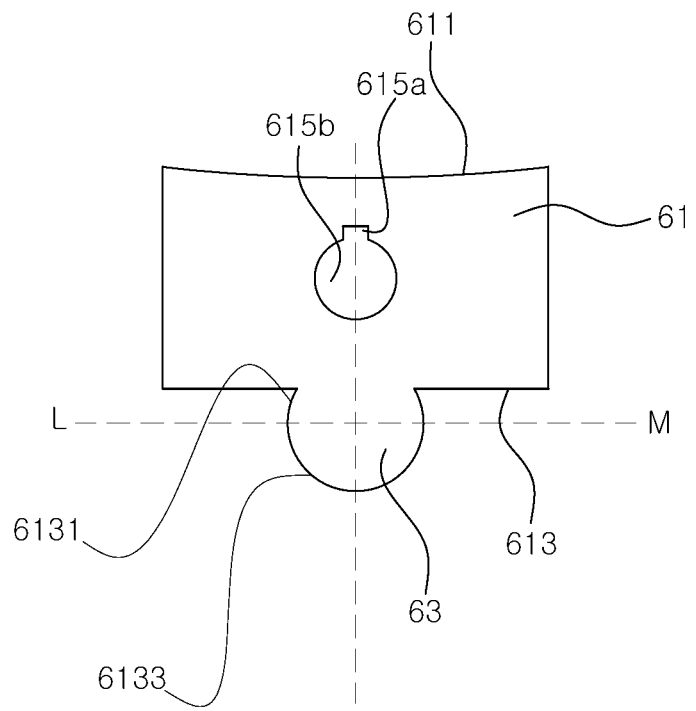
FIG. 27A is a front view illustrating the trial knee joint implant of FIG. 25.
Figure 27B:
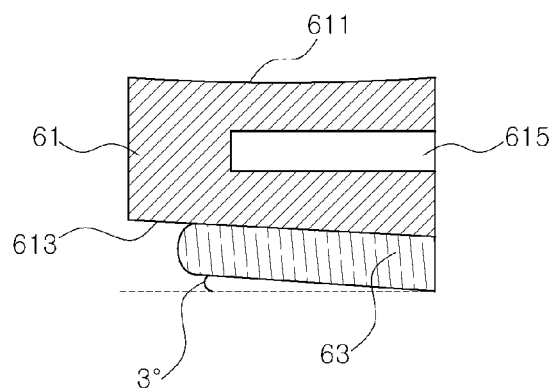
FIG. 27B is a cross-sectional view taken along a line A-A' of FIG. 27A.

The contact surface 613 is disposed on the opposite side of the articular surface 611 and is a portion to be in contact with the tibia 10. The contact surface 613 is an inclined surface inclined by a predetermined angle to enable checking for slope kinematics before the femur 20 is resected. For example, when the results of checking show good kinematics, with the contact surface 613 inclined by an angle of 3☐ as illustrated in FIG. 27B, the tibia or the posterior femoral condyle is additionally resected to increase a flexion gap while maintaining an extension gap.

The guide hole 615 is a hole extending from the anterior side to the posterior side of the body portion 61. As illustrated in FIG. 27A, the guide hole 615 is preferably formed like a key hole. Specifically, the guide hole 615 may include a circular opening 615b and a rectangular opening 615a provided at the top of the circular opening 615a. The guide hole 615 is used to connect a surgical instrument with the trial knee joint implant 6. In this case, the surgical instrument may have a portion having a complementary shape to the guide hole 615 so as to fit the guide hole 65. When the guide hole 615 has a key hole-like shape, since rotation of a member fitted into the guide hole 615 is prevented, stable engagement between the trial knee joint implant and the surgical instrument can be achieved. The guide hole 615 may have any shape that can prevent rotation of a member engaged with the guide hole 615.

With reference to FIG. 26C, a shallow groove (also referred to as a slot cut) 1001 is formed below a bone island 1000. A device for forming the shallow groove 1001 may be connected by a device engaged with the guide holes 615 of the trial knee joint implant 6, which are disposed at opposite sides of the bone island 1000. Accordingly, according to the present invention, a pair of BCR tibial components (not illustrated) having a similar shape to the UKA tibial component 70 and disposed at respective sides of the bone island 1000 can be engaged with the tibia. The pair of BCR tibial components are connected to each other by a connection member (not illustrated) having a shape corresponding to the shallow groove (i.e. slot cut) 1001. Therefore, in the case of using BCR tibial components, since the bone island 1000 can be formed to extend over an overall length, i.e. from an anterior end to a posterior end of the tibia, it is possible to solve the problem of the stress increasing at corners.

The protrusion 63 is formed to protrude from the contact surface 613 and includes a portion expanded sideways. Therefore, the protrusion 63 is fixed by being inserted into the sliding groove of the tibia 10 in a sliding manner. The features of the protrusion 63 are substantially the same as those of the protrusion 604 of the UKA tibial component 60 described above. That is, the shape of the protrusion 63 corresponds to the shape of the sliding groove S formed in the surface of the tibia 10. Specifically, as illustrated in FIG. 27A, the protrusion 63 may includes a first portion 6131 protruding from the contact surface 613 and being gradually expanded sideways such that its transverse width gradually increases and a second portion 6133 protruding from the first portion 6131 and being gradually constricted sideways such that its transverse width gradually decreases. The first portion 6131 and the second portion 6133 have curved peripheral surfaces, and the curved peripheral surfaces form a circular cylinder shape.

As described above, since the protrusion 63 has a shape that can be fitted into the sliding groove S formed in the resected surface of the tibia 10, it is not necessary to form an additional hole in a bone to the combine the trial knee joint implant 6 with the bone, and it is possible to simplify a surgical procedure and reduce a surgery time.

Figure 28:
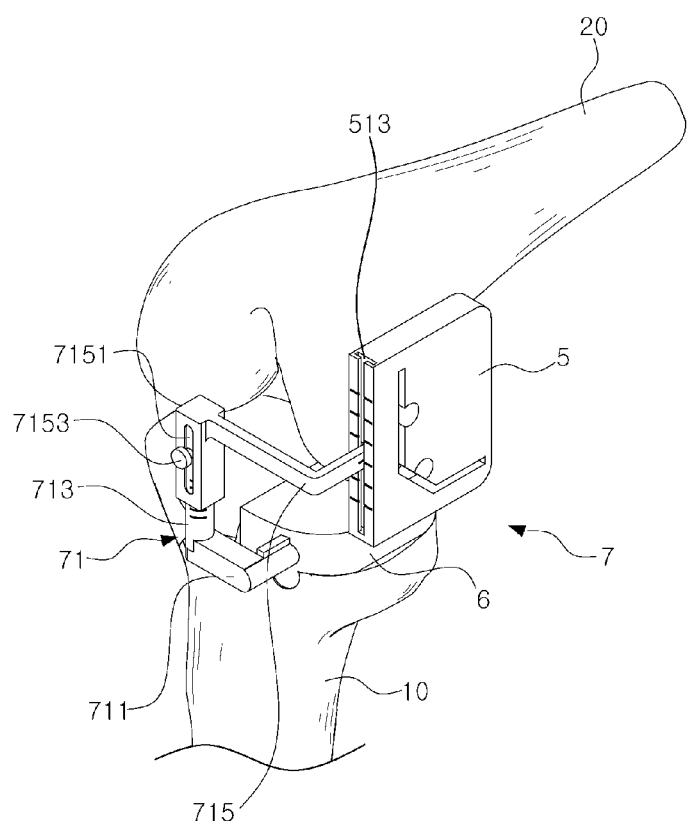
FIG. 28 is a perspective view illustrating a surgical instrument for knee arthroplasty, according to a first embodiment of the present invention.

With reference to FIG. 28, a surgical instrument 7 for knee arthroplasty, according to one embodiment, includes a trial knee joint implant 6, a resection guide 5, and a link mechanism 71.

According to the embodiment of the present invention, the surgical instrument 7 for knee arthroplasty is used to check for flexion and extension of the femur 20 using the trial knee joint implant 6 after the tibia 10 is resected and before the femur 20 is resected, and to enable resection of the femur 20 by attaching the resection guide 5 to the trial knee joint implant 6.

As described above, the trial knee joint implant 6 is a component to be engaged with the sliding groove formed in the resected surface of the tibia 10 to provide a function of checking for kinematics before the femur 20 is resected. In addition, the trial knee joint implant 6 enables fixation and appropriate arrangement of the resection guide 5 in conjunction with the link mechanism 71.

AS illustrated in FIG. 22, the resection guide 5 is a component used to guide resection of the distal end of the femur 20 during UKA or TKA surgery. The detailed structure thereof is the same as the structure described above.

As to the link mechanism 71, a first end thereof is engaged with the guide hole 615 of the trial knee joint implant 6, and a second end thereof is engaged with the main body of the resection guide 5, thereby enabling the main body 51 of the resection guide 5 to be arranged on the lateral surface or the medial surface of the femur 20. The link mechanism 71 includes an engagement protrusion 711, a support portion 713, and a connection portion 715.

The engagement protrusion 711 provides supporting force by engaging with the guide hole 615, and the support portion 713 transfers the supporting force of the engagement protrusion 711 by protruding upward from the engagement protrusion 711. The connection portion 715 connects the support portion 713 with the resection guide 5 such that the resection guide 5 can be arranged on the lateral surface or the medial surface of the femur 20.

With reference to FIG. 28, the link mechanism further includes a height adjustment portion that adjusts the height of the main body. The connection portion 715 is engaged with the support portion 713 such that it can be moved up and down by means of a window 7151 extending in a vertical direction and a knob clamping device 7153. That is, the height adjustment portion includes the window 7151 having a through hole form and the knob clamping device 7153. When the knob clamping device 7153 is loosened, the connection portion 715 can be moved up and down. However, when the knob clamping device 7153 is tightened, the position of the connection portion 715 is fixed.

A second portion of the connection portion 715 is fitted in the slit-like recess 513 that is vertically elongated and formed on the anterior surface of the resection guide 5 such that the height of the main body 51 of the resection guide 5 can be adjusted.

Figure 29:
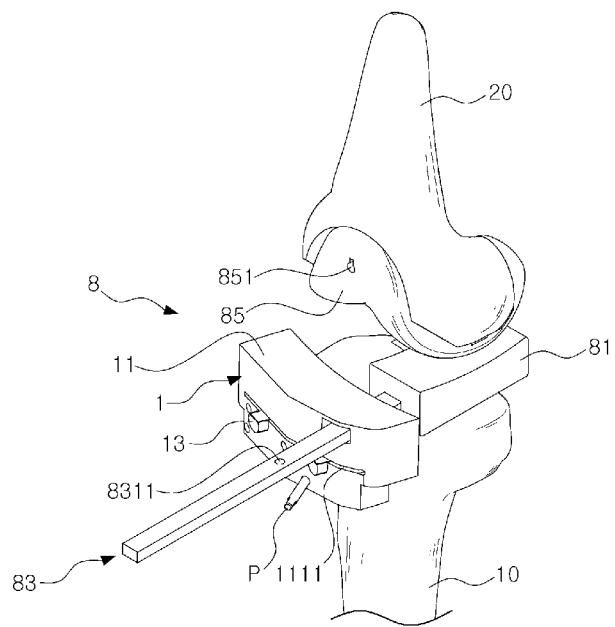
FIG. 29 is a perspective view illustrating a surgical instrument for knee arthroplasty, according to a second embodiment of the present invention.

With reference to FIG. 29, a surgical instrument 8 for knee arthroplasty, according to a second embodiment, includes a spacer 81, an alignment handle 83, and a resection guide 1.

The surgical instrument 8 according to the second embodiment is used in such a manner that a gap between the distal end of the femur 20 and the proximal end of the tibia 10, which occurs due to a ligament release, is checked with the spacer 81 in a state in which a femoral component 85 of a trial knee joint implant is attached to the distal end of the femur 20 and the proximal end of the tibia 10 is not yet resected. In addition, when the surgical instrument 8 is combined with the alignment handle 83, it is possible to appropriately align the resection guide to resect the tibia 10.

Figure 30:
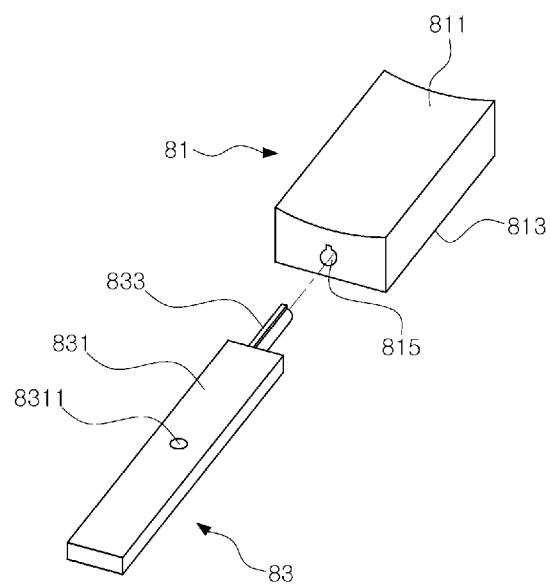
FIG. 30 is a perspective view illustrating a spacer and an alignment handle.

With reference to FIG. 30, the spacer 81 is a device to check the gap between the distal end of the femur 20 and the proximal end of the tibia 10. The spacer 81 enables checking of the gap between the distal end of the femur 20 and the proximal end of the tibia 10, which occurs due to a ligament release, before the tibia 10 is resected. The spacer 81 has an upper surface 811 coming into contact with the femoral component 85, a lower surface 813 coming into contact with the proximal end of the tibia 10, and an engagement recess 815.

As the spacer 81, a plurality of spacers with various thicknesses is prepared to deal with various gap sizes. The upper surface 811 is concavely curved to increase a contact area when it comes into contact with the femoral component 85. The engagement recess 815 may have a key hole-like shape.

As illustrated in FIG. 30, the alignment handle 83 is an elongated member having a first end engaged with the engagement recess 815 of the spacer 81 and a second end protruding from the front surface of the spacer 81. The alignment handle 83 includes a body portion 831 having a bar-like shape and an engagement protrusion 833 shaped to engage with the engagement recess 815 and provided at the front surface of the body portion 831. The engagement protrusion 833 is inserted into the engagement recess 815 such that the alignment handle 83 is stably combined with the spacer 81.

Figure 31:
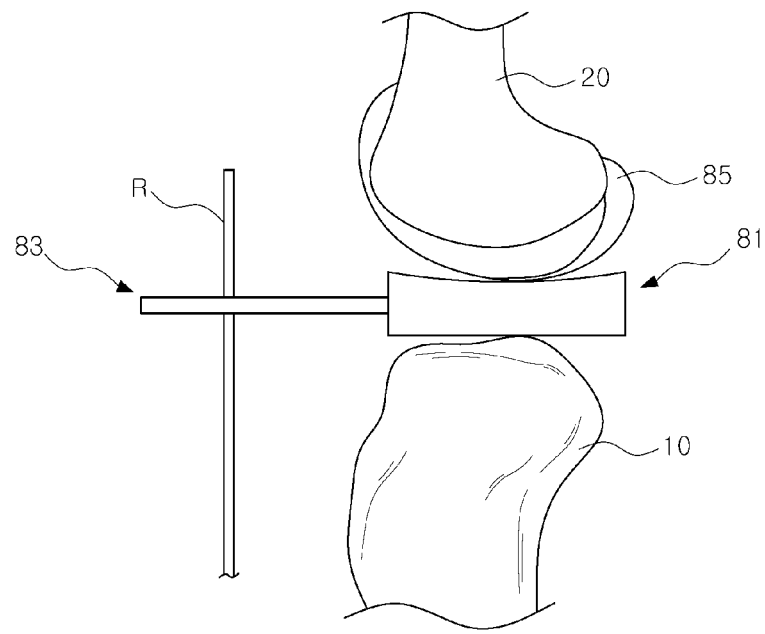
FIG. 31 is a view illustrating a process of EM alignment check using the spacer and the alignment handle.

The alignment handle 83 is arranged to pass through the window 113 of the resection guide 1, thereby fixing the main body of the resection guide 1 in place. Therefore, the body portion 831 of the alignment handle 83 preferably has a shape corresponding to that of the window 133 such that the main body of the resection guide is stably fixed and thus the resection of a bone is reliably guided by the resection guide. The body portion 831 is provided with an insertion hole 8311 that vertically extends through the body portion 831 and through which an EM alignment rod R passes. Accordingly, as illustrated in FIG. FIG. 31, it is possible to verify alignment of the resection guide with the use of an EM alignment rod R.

The resection guide of the surgical instrument 8 for knee arthroplasty, according to the second embodiment, may be the resection guide 3 that is used to resect the proximal end of the tibia during UKA rather than the resection guide 1 that is used to resect the tibia 10 during TKA.

Figure 32A:
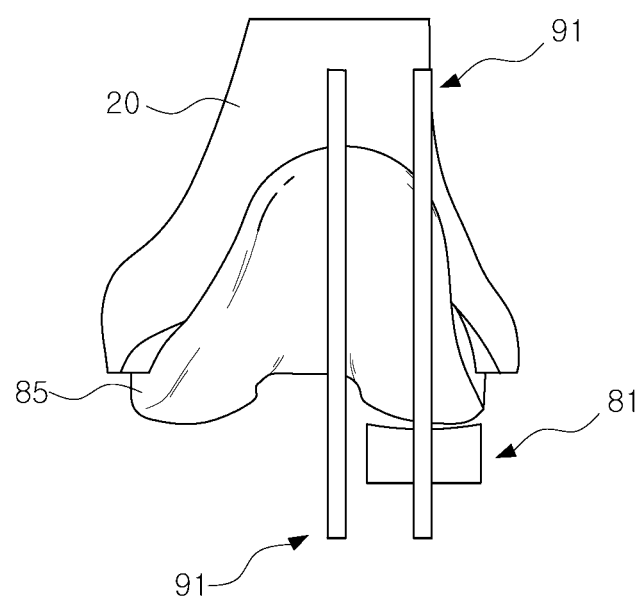
FIGS. 32A and 32B are a front view and an exploded perspective view of a surgical instrument for knee arthroplasty, according to a third embodiment of the present invention.
Figure 32B:
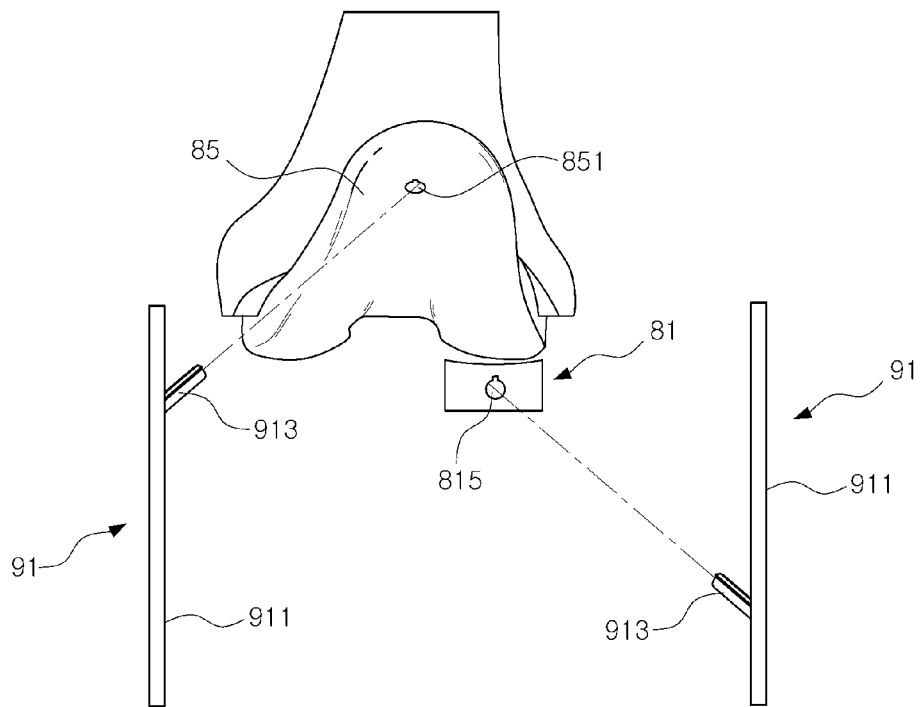

With reference to FIGS. 32A and 32B, a surgical instrument 9 for knee arthroplasty according to a third embodiment includes two horizontal alignment rods 9 and a spacer 81.

The surgical instrument 9 for knee arthroplasty according to the third embodiment is used such that a gap between the distal end of the femur 20 and the proximal end of the tibia 10 is checked with the spacer 81 in a state in which the femoral component 85 of the trial knee joint implant is attached to the distal end of the femur 20 and the proximal end of the tibia 10 is not yet resected, and alignment of a knee joint can be verified using the two horizontal alignment rods 91.

The horizontal alignment rod 91 includes an arrangement portion 911 (i.e. a linearly elongated member) and an engagement protrusion 913 perpendicularly protruding from the alignment portion 911. The engagement protrusion 913 has a shape corresponding to that of an engagement recess 815 such that the engagement protrusion 913 can be inserted into the engagement recess 815.

Figure 33:
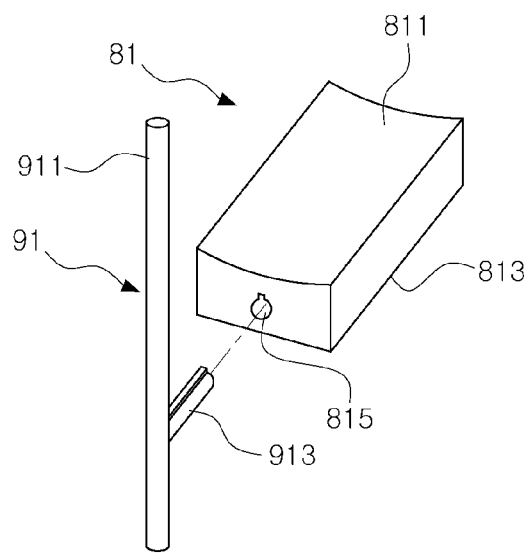
FIG. 33 is a perspective view illustrating a spacer and a horizontal alignment rod.

With reference to FIG. 33, the horizontal alignment rod 91 can be engaged with the engagement recess 815 of the spacer 81 instead of the alignment handle 83. With reference to FIGS. 32A and 32B, the horizontal alignment rod 91 may be engaged with the key hole 851 formed at the anterior surface of the femoral component 85 of the trial knee joint implant.

The horizontal alignment rod 91 is arranged to be perpendicular to the distal surface of the femur 20 in a state in which the horizontal alignment rod 91 is engaged with the key hole 851. When one horizontal alignment rod 91 is engaged with the engagement recess 815 of the spacer 81 that is inserted between the distal end of the femur 20 and the proximal end of the tibia 10 in a state in which the other horizontal alignment rod 91 is engaged with the key hole 851 of the femoral component 85, alignment of a knee joint on the coronal plane can be checked. That is, when the two horizontal alignment rods 91 are parallel to each other on the coronal plane, it is considered that the knee joint is well aligned on the coronal plane. In this state, alignment on the sagittal plane is not yet achieved. This is because, the proximal end of the tibia 10 is not yet resected and thus has a curved native surface.

Although various embodiments of the present invention have been described for illustrative purposes, those skilled in the art will appreciate that various modifications, additions, and substitutions are possible, without departing from the scope and spirit of the invention as disclosed in the accompanying claims.

What is claimed is:

1. A surgical instrument system for knee arthroplasty, the surgical instrument system comprising:
    a femoral component of a trial knee joint implant configured to engage with a distal end of a femur, the femoral component being provided with an engagement recess at an anterior surface thereof;
    a spacer configured to be inserted between the distal end of the femur and a proximal end of a tibia, the spacer having an upper surface configured to contact the femoral component, a lower surface configured to contact a proximal end of the tibia, and an engagement recess provided at an anterior surface of the spacer; and
    two horizontal alignment rods, each comprising an alignment portion that is a linearly elongated member and an engagement protrusion that extends perpendicularly to the alignment portion,
    wherein one of the two horizontal alignment rods is arranged such that the engagement protrusion of the horizontal alignment rod is engaged with the engagement recess of the femoral component,
    the other horizontal alignment rod is arranged such that the engagement protrusion of the horizontal alignment rod is engaged with the engagement recess of the spacer, and
    wherein an aligned state of a knee joint can be verified by checking whether the two horizontal alignment rods are parallel with each other on a coronal plane.

2. The surgical instrument system of claim 1, wherein each engagement recess and each respective engagement protrusion are configured to engage one another in a complementary mating relationship.

3. The surgical instrument system of claim 1, wherein the spacer has a thickness separating the upper surface and the lower surface thereof, and wherein said thickness approximates a natural anatomical spacing between the distal end of the femur and the proximal end of the tibia.

4. The surgical instrument system of claim 3, wherein the upper surface of the spacer has a concave shape.

5. The surgical instrument system of claim 4, wherein the lower surface of the spacer is substantially planar.

6. The surgical instrument system of claim 3, wherein the spacer comprises a plurality of spacers having different thicknesses.

7. The surgical instrument system of claim 3, wherein each engagement recess and each respective engagement protrusion further comprise complementary interlocking portions to allow mating engagement while fixing a rotational position of the engagement protrusion relative to the engagement recess.

8. The surgical instrument system of claim 7, wherein the complementary interlocking portions comprise complementary key-way components.

9. A surgical instrument system for use in achieving and maintaining the a proper spacing, orientation and alignment of a femur and tibia relative to one another on a coronal plane, the surgical instrument system comprising:
  a femoral implant component configured to be applied to a distal end of a resected femur;
  a spacer configured to be inserted between the femoral implant component and a proximal end of the tibia, the spacer having an upper surface for contacting the femoral implant component, a lower surface for contacting the proximal end of the tibia, and a first engagement recess provided at an anterior surface of the spacer; and
  first and second alignment rods, each comprising a linearly elongated alignment portion and an engagement protrusion that extends perpendicularly to the alignment portion.

10. The surgical instrument system of claim 9, wherein the femoral implant component is provided with a second engagement recess at an anterior surface thereof.

11. The surgical instrument system of claim 10, wherein the engagement protrusion of the first alignment rod engages the first engagement recess of the spacer, and
  wherein the engagement protrusion of the second alignment rod engages the second engagement recess of the femoral implant component.

12. The surgical instrument system of claim 11, wherein the relative placement and orientation of the first and second engagement recesses are such that a properly oriented and aligned state of the knee joint on the coronal plane is indicated when the two alignment rods are parallel to one another.

13. The surgical instrument system of claim 12, wherein the spacer has a thickness separating the upper surface and the lower surface thereof, and wherein said thickness approximates a natural anatomical spacing between the distal end of the femur and the proximal end of the tibia.

14. The surgical instrument system of claim 13, wherein the upper surface of the spacer has a concave shape.

15. The surgical instrument system of claim 14, wherein the lower surface of the spacer is substantially planar.

16. The surgical instrument system of claim 12, wherein the spacer comprises a plurality of interchangeable spacers having different thicknesses.

17. The surgical instrument system of claim 12, wherein the first engagement recess and the engagement protrusion of the first alignment rod are configured to engage one another in a complementary mating relationship, and
  wherein the second engagement recess and the engagement protrusion of the second alignment rod are configured to engage one another in a complementary mating relationship.

18. The surgical instrument system of claim 17, wherein the first engagement recess and the engagement protrusion of the first alignment rod further comprise complementary interlocking portions to allow mating engagement while fixing the rotational position of the first alignment rod relative to the first engagement recess and the spacer, and
  wherein the second engagement recess and the engagement protrusion of the second alignment rod further comprise complementary interlocking portions to allow mating engagement while fixing the rotational position of the second alignment rod relative to the second engagement recess and the femoral implant component.

19. The surgical instrument system of claim 18, wherein the complementary interlocking portions comprise complementary key-way components.

20. A surgical instrument system for use in achieving and maintaining a proper spacing, orientation and alignment of a femur and tibia relative to one another on a coronal plane, the surgical instrument system comprising:
  a femoral implant component configured to be applied to a distal end of a resected femur, the femoral implant component being provided with a second engagement recess at an anterior surface thereof;
  a spacer configured to be inserted between the femoral implant component and a proximal end of a tibia, the spacer having an upper surface for contacting the femoral implant component, a lower surface for contacting the proximal end of the tibia, a first engagement recess provided at an anterior surface of the spacer, and a thickness approximating a natural anatomical spacing between the distal end of the femur and the proximal end of the tibia; and
  first and second alignment rods, each comprising a linearly elongated alignment portion and an engagement protrusion that extends perpendicularly to the alignment portion,
  wherein the engagement protrusion of the first alignment rod engages the first engagement recess of the spacer,
  wherein the engagement protrusion of the second alignment rod engages the second engagement recess of the femoral implant component, and
  wherein the relative placement and orientation of the first and second engagement recesses are such that a properly oriented and aligned state of the knee joint on the coronal plane can be indicated when the two alignment rods are parallel to one another.

* * * * *